US011109833B2

(12) United States Patent
Nystrom et al.

(10) Patent No.: US 11,109,833 B2
(45) Date of Patent: Sep. 7, 2021

(54) POSITION SENSING IN INTRAVASCULAR PROCESSES

(71) Applicant: ACIST Medical Systems, Inc., Eden Prairie, MN (US)

(72) Inventors: Sidney Donald Nystrom, Shoreview, MN (US); Kendall R. Waters, Sammamish, WA (US); Edward R. Miller, Eden Prairie, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 367 days.

(21) Appl. No.: 15/599,000

(22) Filed: May 18, 2017

(65) Prior Publication Data

US 2017/0333000 A1 Nov. 23, 2017

Related U.S. Application Data

(60) Provisional application No. 62/338,885, filed on May 19, 2016.

(51) Int. Cl.
*A61B 8/12* (2006.01)
*A61B 5/06* (2006.01)
(Continued)

(52) U.S. Cl.
CPC .............. *A61B 8/12* (2013.01); *A61B 5/0084* (2013.01); *A61B 5/0215* (2013.01); *A61B 5/062* (2013.01);
(Continued)

(58) Field of Classification Search
CPC ....... A61B 5/062; A61B 8/4254; A61B 90/39; A61B 2090/3954; A61B 2034/2051;
(Continued)

(56) References Cited

U.S. PATENT DOCUMENTS

| 4,756,313 A | 7/1988 | Terwilliger |
| 5,244,461 A | 9/1993 | Derlien |

(Continued)

FOREIGN PATENT DOCUMENTS

| AU | 2013201648 B2 | 4/2014 |
| CN | 101687087 A | 3/2010 |

(Continued)

OTHER PUBLICATIONS

International Patent Application No. PCT/US2017/033332, International Search Report & Written Opinion dated Jul. 28, 2017, 13 pages.

(Continued)

*Primary Examiner* — Keith M Raymond
*Assistant Examiner* — Milton Truong
(74) *Attorney, Agent, or Firm* — Fredrikson & Byron, P.A.

(57) ABSTRACT

Intravascular systems can include a catheter having a proximal end, a distal end, a sensor located at the distal end configured to provide sensor information representative of one or more intravascular properties of a patient, and a plurality of magnetic domains. A magnetic pickup can be configured to output a pickup signal based on the magnetic field at the magnetic pickup produced by the plurality of magnetic domains. An intravascular processing engine can be in communication with the catheter sensor and the magnetic pickup. The intravascular processing engine can receive sensor information from the sensor and a position signal representative of the pickup signal. The intravascular processing engine can be used to determine position information related to the position of the catheter sensor and combine the received sensor information and corresponding determined position information.

18 Claims, 13 Drawing Sheets

(51) Int. Cl.
*A61B 8/00* (2006.01)
*A61B 5/0215* (2006.01)
*A61B 8/06* (2006.01)
*A61B 8/08* (2006.01)
*A61B 8/04* (2006.01)
*A61B 5/00* (2006.01)
*G01S 15/89* (2006.01)

(52) U.S. Cl.
CPC .............. *A61B 8/04* (2013.01); *A61B 8/06* (2013.01); *A61B 8/085* (2013.01); *A61B 8/0891* (2013.01); *A61B 8/4254* (2013.01); *A61B 8/445* (2013.01); *A61B 8/483* (2013.01); *A61B 8/5207* (2013.01); *G01S 15/899* (2013.01); *A61B 8/44* (2013.01); *G01S 15/89* (2013.01)

(58) Field of Classification Search
CPC ........... A61B 1/00158; A61B 1/00154; A61M 25/0127; A61M 25/09; A61M 25/0662; A61M 25/065
See application file for complete search history.

(56) References Cited

U.S. PATENT DOCUMENTS

| | | | |
|---|---|---|---|
| 5,327,885 A | 7/1994 | Griffith | |
| 5,361,768 A | 11/1994 | Webler et al. | |
| 5,827,313 A | 10/1998 | Ream et al. | |
| 5,908,395 A | 6/1999 | Stalker et al. | |
| 6,004,269 A | 12/1999 | Crowley et al. | |
| 6,004,271 A | 12/1999 | Moore et al. | |
| 6,035,229 A | 3/2000 | Silverstein et al. | |
| 6,226,546 B1 | 5/2001 | Evans | |
| 6,251,078 B1 | 6/2001 | Moore et al. | |
| 6,263,230 B1* | 7/2001 | Haynor .................. | A61B 5/062 128/899 |
| 6,292,681 B1 | 9/2001 | Moore | |
| 6,319,227 B1 | 11/2001 | Mansouri-Ruiz | |
| 6,321,106 B1 | 11/2001 | Lemelson | |
| 6,398,755 B1 | 6/2002 | Belef et al. | |
| 6,511,432 B2 | 1/2003 | Moore et al. | |
| 6,592,520 B1 | 7/2003 | Peszynski et al. | |
| 6,974,465 B2 | 12/2005 | Belef et al. | |
| 8,157,741 B2 | 4/2012 | Hirota | |
| 8,298,156 B2 | 10/2012 | Manstrom et al. | |
| 9,138,248 B2 | 9/2015 | Sliwa et al. | |
| 9,492,638 B2 | 11/2016 | McKinnis et al. | |
| 2001/0021841 A1 | 9/2001 | Webler et al. | |
| 2001/0045935 A1 | 11/2001 | Chang et al. | |
| 2001/0047165 A1 | 11/2001 | Makower et al. | |
| 2002/0047367 A1 | 4/2002 | Kim et al. | |
| 2002/0050169 A1 | 5/2002 | Ritter et al. | |
| 2002/0093880 A1 | 7/2002 | Nakamura | |
| 2002/0107447 A1 | 8/2002 | Suorsa et al. | |
| 2002/0183723 A1 | 12/2002 | Belef et al. | |
| 2003/0013958 A1 | 1/2003 | Govari et al. | |
| 2003/0135995 A1 | 7/2003 | Glasson | |
| 2003/0171678 A1 | 9/2003 | Batten et al. | |
| 2003/0187369 A1 | 10/2003 | Lewis et al. | |
| 2004/0078036 A1 | 4/2004 | Keidar | |
| 2004/0097803 A1 | 5/2004 | Panescu | |
| 2004/0133105 A1 | 7/2004 | Ostrovsky et al. | |
| 2004/0147920 A1 | 7/2004 | Keidar | |
| 2004/0215130 A1 | 10/2004 | Rioux et al. | |
| 2005/0054929 A1 | 3/2005 | Angelsen et al. | |
| 2006/0031953 A1 | 2/2006 | Cheah | |
| 2006/0106375 A1 | 5/2006 | Werneth et al. | |
| 2006/0122514 A1 | 6/2006 | Byrd et al. | |
| 2006/0224153 A1 | 10/2006 | Fischell et al. | |
| 2006/0241445 A1 | 10/2006 | Altmann et al. | |
| 2006/0241469 A1 | 10/2006 | Rold et al. | |
| 2006/0241484 A1 | 10/2006 | Horiike et al. | |
| 2006/0287599 A1 | 12/2006 | Cimino | |
| 2007/0014445 A1 | 1/2007 | Lin | |
| 2007/0066890 A1 | 3/2007 | Maschke | |
| 2007/0093752 A1 | 4/2007 | Zhao et al. | |
| 2007/0106147 A1 | 5/2007 | Altmann et al. | |
| 2007/0135803 A1* | 6/2007 | Belson ............... | A61B 17/3462 606/1 |
| 2007/0167752 A1 | 7/2007 | Proulx et al. | |
| 2007/0167821 A1 | 7/2007 | Lee et al. | |
| 2008/0146941 A1 | 6/2008 | Dala-Krishna | |
| 2008/0154131 A1 | 6/2008 | Lee et al. | |
| 2008/0177180 A1 | 7/2008 | Azhari et al. | |
| 2008/0195041 A1 | 8/2008 | Goldfarb et al. | |
| 2008/0200801 A1 | 8/2008 | Wildes et al. | |
| 2008/0255449 A1 | 10/2008 | Warnking et al. | |
| 2008/0255475 A1* | 10/2008 | Kondrosky .......... | A61M 25/09 600/585 |
| 2009/0054776 A1 | 2/2009 | Sasaki | |
| 2009/0069693 A1 | 3/2009 | Burcher et al. | |
| 2009/0088628 A1 | 4/2009 | Klingenbeck-Regn | |
| 2009/0124998 A1 | 5/2009 | Rioux et al. | |
| 2009/0137952 A1 | 5/2009 | Ramamurthy et al. | |
| 2009/0156941 A1 | 6/2009 | Moore | |
| 2009/0234220 A1 | 9/2009 | Maschke | |
| 2009/0234302 A1 | 9/2009 | Hoendervoogt et al. | |
| 2009/0234445 A1 | 9/2009 | Maschke | |
| 2010/0057019 A1 | 3/2010 | Zelenka | |
| 2010/0152590 A1* | 6/2010 | Moore ..................... | A61B 8/12 600/466 |
| 2010/0179434 A1 | 7/2010 | Thornton | |
| 2010/0249603 A1 | 9/2010 | Hastings et al. | |
| 2011/0021924 A1 | 1/2011 | Sethuraman et al. | |
| 2011/0184406 A1* | 7/2011 | Selkee ................. | A61B 5/6885 606/41 |
| 2011/0230906 A1* | 9/2011 | Modesitt .................. | A61B 1/04 606/185 |
| 2012/0071752 A1 | 3/2012 | Sewell et al. | |
| 2012/0150035 A1 | 6/2012 | Seip et al. | |
| 2013/0039294 A1 | 2/2013 | Wang | |
| 2013/0137963 A1 | 5/2013 | Olson | |
| 2013/0172713 A1 | 7/2013 | Kirschenman | |
| 2013/0211436 A1 | 8/2013 | Larson et al. | |
| 2013/0274657 A1 | 10/2013 | Zirps et al. | |
| 2014/0039294 A1 | 2/2014 | Jiang | |
| 2014/0163361 A1 | 6/2014 | Stigall et al. | |
| 2014/0180127 A1 | 6/2014 | Meyer et al. | |
| 2014/0343433 A1 | 11/2014 | Elbert | |
| 2015/0038824 A1 | 2/2015 | Lupotti | |
| 2015/0065956 A1* | 3/2015 | Huang ................. | A61M 5/5086 604/111 |
| 2015/0182190 A1* | 7/2015 | Hiltner .................. | A61B 5/743 600/463 |
| 2016/0081657 A1* | 3/2016 | Rice ....................... | A61B 8/445 600/301 |
| 2016/0220314 A1* | 8/2016 | Huelman ............... | A61B 34/20 |
| 2017/0333000 A1 | 11/2017 | Nystrom et al. | |

FOREIGN PATENT DOCUMENTS

| | | |
|---|---|---|
| CN | 103037759 A | 4/2013 |
| CN | 103037761 A | 4/2013 |
| CN | 202876024 U | 4/2013 |
| CN | 103385706 A | 11/2013 |
| CN | 103635146 A | 3/2014 |
| CN | 105025787 A | 11/2015 |
| EP | 1929954 A1 | 6/2008 |
| EP | 1952768 A2 | 8/2008 |
| EP | 2358278 A2 | 8/2011 |
| EP | 2749240 A2 | 7/2014 |
| JP | S63122923 A | 5/1988 |
| JP | S63281632 A | 11/1988 |
| JP | S63302836 A | 12/1988 |
| JP | H0417843 A | 1/1992 |
| JP | H05244694 A | 9/1993 |
| JP | H078497 A | 1/1995 |
| JP | H0795980 A | 4/1995 |
| JP | H07136171 A | 5/1995 |
| JP | H07184902 A | 7/1995 |
| JP | H07508204 A | 9/1995 |

(56) References Cited

FOREIGN PATENT DOCUMENTS

| | | |
|---|---|---|
| JP | H08112286 A | 5/1996 |
| JP | 2000157546 A | 6/2000 |
| JP | 2002301070 A | 10/2002 |
| JP | 2003265483 A | 9/2003 |
| JP | 2004209277 A | 7/2004 |
| JP | 2005507273 A | 3/2005 |
| JP | 2005536289 A | 12/2005 |
| JP | 2006102240 A | 4/2006 |
| JP | 2007044074 A | 2/2007 |
| JP | 2007105450 A | 4/2007 |
| JP | 2007152094 A | 6/2007 |
| JP | 2007268132 A | 10/2007 |
| JP | 2008053887 A | 3/2008 |
| JP | 2008155022 A | 7/2008 |
| JP | 2008178676 A | 8/2008 |
| JP | 2008277834 A | 11/2008 |
| JP | 2008539887 A | 11/2008 |
| JP | 2012510885 A | 5/2012 |
| WO | 9203095 A1 | 3/1992 |
| WO | 2003011139 A1 | 2/2003 |
| WO | 2007044792 A1 | 4/2007 |
| WO | 2008042423 A2 | 4/2008 |
| WO | 2008086613 A1 | 7/2008 |
| WO | 2010077632 A2 | 7/2010 |
| WO | 2010107916 A1 | 9/2010 |
| WO | 2011058493 A1 | 5/2011 |
| WO | 2015073817 A1 | 5/2015 |
| WO | 2015102573 A1 | 7/2015 |

OTHER PUBLICATIONS

Baello, et al., "Ultrasound Study of Acoustic Properties of the Normal Canine Heart: Comparison of Backscatter From all Chambers," JACC vol. 8, No. 4, Oct. 1985:880-4.

* cited by examiner

POSITION SENSING IN INTRAVASCULAR PROCESSES

PRIORITY CLAIM

This application claims priority to U.S. provisional patent application No. 62/338,885 filed May 19, 2016.

TECHNICAL FIELD

This disclosure relates to an intravascular system and a method of operating the same.

BACKGROUND

Intravascular processes such as imaging processes or receiving other physiological measurements (e.g., measurements of blood parameters, such as blood pressure, oxygen saturation levels, blood pH, etc.) are often used to identify diagnostically significant characteristics of a vessel. For example, an intravascular imaging system may be used by a healthcare professional to help identify and locate blockages or lesions in a vessel. Common intravascular imaging systems include intravascular ultrasound (IVUS) systems as well as optical coherence tomography (OCT) systems.

Intravascular imaging involves one or more transducers emitting and/or receiving energy based on received electrical signals and sending return electrical signals based on signals reflected by various intravascular structures. Intravascular imaging is often used to generate images. In some instances, a console with a high-resolution display is able to display intravascular images in real-time. In this way, intravascular imaging can be used to provide in-vivo visualization of the vascular structures and lumens, including the coronary artery lumen, coronary artery wall morphology, and devices, such as stents, at or near the surface of the coronary artery wall. Intravascular imaging may be used to visualize diseased vessels, including coronary artery disease. In some instances, the transducer(s) can be carried near a distal end of an intravascular imaging catheter. Some intravascular imaging systems involve rotating the intravascular imaging catheter (e.g., mechanically, phased-array, etc.) for 360-degree visualization.

Many intravascular imaging systems are configured to perform translation operations, in which imaging components of the catheter are translated through a patient's blood vessel while acquiring images. The result is a 360-degree image with a longitudinal component. When performing a translation operation, it can be important to accurately determine at least the relative amount of translation of the catheter's imaging components in order to accurately construct the 360-degree image.

In other intravascular processes, intravascular blood pressure measurements may be used for evaluating the degree to which a stenotic lesion obstructs flow through a blood vessel, such as a Fractional Flow Reserve measurement (FFR). To calculate the FFR for a given stenosis, two blood pressure readings are taken using a pressure sensor, such as a monorail pressure sensor (MPS). One pressure reading is taken on the distal side of the stenosis (e.g., downstream from the stenosis), the other pressure reading is taken on the proximal side of the stenosis (e.g., upstream from the stenosis, towards the aorta). The FFR is defined as the ratio of maximal blood flow in a stenotic artery, taken distal to the lesion, to normal maximal flow, and is typically calculated based on a measured pressure gradient of the distal pressure to the proximal pressure. The FFR is therefore a unitless ratio of the distal and proximal pressures. The pressure gradient, or pressure drop, across a stenotic lesion is an indicator of the severity of the stenosis, and the FFR is a useful tool in assessing the pressure drop. The more restrictive the stenosis is, the greater the pressure drop, and the lower the resulting FFR. The FFR measurement may be a useful diagnostic tool.

One method of measuring the pressure gradient across a lesion is to use a small catheter connected to a blood pressure measurement sensor. The catheter would be passed over the guidewire which has already been placed across the lesion. The catheter would be advanced down the guidewire until the tip of the catheter crosses the lesion. The blood pressure on the distal side of the lesion is recorded. This pressure would be divided by the pressure value recorded in the aorta. A disadvantage of using this method is that some error may be introduced due to the cross sectional size of the catheter. As the catheter crosses the lesion, the catheter itself introduces blockage, in addition to that caused by the lesion itself. The measured distal pressure would therefore be somewhat lower than it would be without the additional flow obstruction, which may exaggerate the measured pressure gradient across the lesion.

Pressure drop can also be measured across a heart valve. When a heart valve is regurgitant, a less than optimal pressure drop is typically observed. Using a catheter to measure pressure drop is common across a heart valve. However, because of the catheter size, the heart valve may not seal well around the catheter. Leakage might also result from the presence of the catheter and may contribute to an inaccurate pressure drop reading. One example of where this could occur is in the mitral valve (e.g., mitral valve regurgitation).

One method of measuring blood pressure in a patient is to use a pressure sensing guidewire. Such a device has a pressure sensor embedded within the guidewire itself. A pressure sensing guidewire can be used in the deployment of interventional devices such as angioplasty balloons or stents. Prior to the intervention, the pressure sensing guidewire would be deployed across a stenotic lesion so the sensing element is on the distal side of the lesion and the distal blood pressure is recorded. The guidewire may then be retracted so the sensing element is on the proximal side of the lesion. The pressure gradient across the stenosis and the resulting FFR value can then be calculated.

To use a guidewire-based pressure sensor in certain applications, the guidewire must be repositioned so the sensing element of the guidewire is correctly placed with respect to a stenotic lesion, for example. Blood pressure measurements for calculating FFR, for example, are generally taken on both sides of a given stenosis, so the guidewire is typically retracted across the stenosis to make the upstream measurement. After retracting the guidewire to make the proximal pressure measurement (aortic pressure or upstream coronary pressure), the guidewire may again be repositioned downstream of the lesion, for example, if it is determined (e.g., based on the FFR calculation) that an interventional device should be deployed. In cases where there are multiple lesions, the sensing element of a pressure sensing guidewire would need to be advanced and retracted across multiple lesions, and would potentially have to be advanced and repositioned again for each such lesion. Advancing and maneuvering a pressure sensing guidewire though stenotic lesions and the vasculature, for example, can be a difficult and/or time consuming task.

In existing systems, the amount of translation or maneuvering of intravascular catheter components is often estimated by attempting to translate portions of the catheter at a certain velocity for a certain amount of time. If the catheter's components are translated at a certain velocity for a certain time, the translated distance can be calculated. However, if the actual translation velocity is not the same as the commanded velocity, for example, or cannot be otherwise reliably measured or produced, inaccuracies in determining the amount of translation can occur. Inaccurate translation determinations can lead to errors in determining position-dependent information of the patient's vasculature. Additionally or alternatively, in some procedures, it may not be necessary or even desirable to pull the catheter back at a fixed velocity. For example, an operator may want to spend more time analyzing areas of interest, or to return to an area of interest by navigating the catheter in the opposite direction. In still further examples, velocity is not measured, and distances may simply be estimated by a system operator. Accordingly, more reliable position sensing mechanism may be useful in performing position-sensitive intravascular processes.

SUMMARY

Aspects of this disclosure include systems and methods for monitoring the position of one or more components of a catheter. Some exemplary systems include a catheter having a proximal end, a distal end, a sensor located at the distal end, and a cable extending from the proximal end of the catheter to the distal end of the catheter. The cable can be operatively connected to the sensor at the distal end, and the sensor can be configured to provide an intravascular signal representative of one or more intravascular properties of a patient. Exemplary sensors can include ultrasound transducers, pressure sensors, or the like.

In some embodiments, the catheter includes one or more magnetic domains, for example, disposed on the cable of the catheter. In various examples, the cable can include a magnetizable material such that the one or more magnetic domains are included in the cable. Additionally or alternatively, such domains can be included in a magnetic coating applied to the cable. In some examples, the one or more magnetic domains comprises a plurality of magnetic domains. In some such embodiments, domains in a subset of the plurality of magnetic domains are distinguishable from domains in a different subset of the plurality of magnetic domains.

The system can further include a magnetic pickup configured to output a pickup signal based on the magnetic field at the magnetic pickup produced by the one or more magnetic domains. In some examples, the pickup can be disposed in a valve, such as a hemostasis valve, through which the catheter translates.

Systems can include an intravascular processing engine in communication with the sensor of the catheter and the magnetic pickup. The intravascular processing engine can be configured to receive sensor information from the catheter sensor and a position signal representative of the pickup signal. The intravascular processing engine can be configured to determine position information related to the position of the catheter sensor based on the received position signal and combine the received sensor information and determined position information.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

The following detailed description should be read with reference to the accompanying drawings, in which like numerals denote like elements. The drawings, which are not necessarily to scale, depict selected embodiments of the invention—other possible embodiments may become readily apparent to those of ordinary skill in the art with the benefit of these teachings. Thus, the embodiments shown in the accompanying drawings and described below are provided for illustrative purposes, and are not intended to limit the scope of the invention as defined in the claims appended hereto.

Embodiments of the invention are generally directed toward position sensing in intravascular processes such as intravascular ultrasound (IVUS) imaging and other parameter sensing applications, for examples, using a monorail pressure sensor (MPS). Such processes typically involve inserting a catheter into the vasculature of a patient for performing at diagnostic and/or therapeutic procedures. Often it is advantageous for a medical practitioner to know at least relative positions of diagnostic or therapeutic elements attached to the catheter within the patient. For example, a diagnostic procedure such as determining pressure gradient across a stenotic lesion may lead to a medical practitioner recommending one or more treatments to be performed based on the diagnostic procedure. In some such examples, the recommended treatment is region-specific, such as placing a stent within the patient's vasculature proximate the region of the measured pressure gradient. In another example, such as in an IVUS system, a series of ultrasound measurements associated with a length of a patient's vasculature may be performed. In such examples, it can be advantageous to know at least the relative positions along the blood vessel with which various image data are associated. Thus, in many situations, it may be advantageous to know at least relative positions associated with measurements and treatments performed intravascularly.

Figure 1:
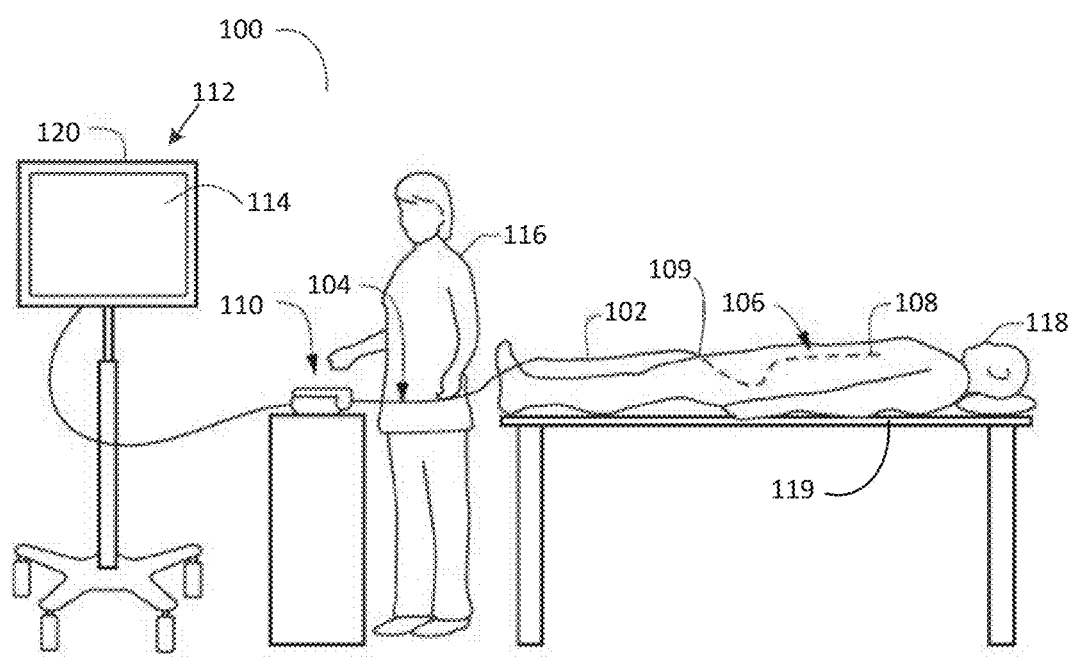
FIG. 1 is an illustrative intravascular system.

FIG. 1 is an illustrative example of a system 100 that may be configured to perform an intravascular procedure. System 100 may include a catheter 102, an interface element 110, and a processing engine 112. The catheter 102 may include a proximal end 104 and a distal end 106 configured to be inserted into a vessel of a patient 118. As shown, patient 118 is positioned on an operating table, which may comprise a surgical mat 119. In one example, catheter 102 may be inserted into the patient 118 via the femoral artery and guided to an area of interest within the patient 118. The broken lines in FIG. 1 represent portions of catheter 102 within the patient 118. In some examples, at least a portion of the catheter 102 is inserted into the patient 118 through a valve 109, such as a hemostasis valve. The valve 109 may be configured to permit catheter access to a patient's vasculature while minimizing or preventing the amount of fluid that may escape the patient's body via the entrance location of the catheter 102.

In some examples, catheter 102 may include a sensor 108 at the distal end 106 that is configured to provide information indicative of an environment within the patient's vasculature. For example, where system 100 is an IVUS system, sensor 108 may comprise an ultrasound transducer configured to emit and receive ultrasound energy and generate ultrasound data. In another imaging example, system 100 may be an OCT system, and sensor 108 may comprise an OCT transducer configured to emit and receive light and generate OCT data. The catheter 102 can be configured to generate image information and transmit that image information in an imaging procedure. In still further examples, sensor 108 may include a pressure transducer for providing a signal representative of patient blood pressure, for example.

Returning to FIG. 1, the interface element 110 of the intravascular imaging system 100 can be engaged with the catheter 102 and can provide an interface with the catheter 102, such as an electrical interface, a mechanical interface, or both. In some embodiments, the interface element 110 may include a translation mechanism configured to translate at least a portion of the catheter 102 a controlled distance within the patient 118 during a pullback or other translation operation. For example, in some embodiments, the catheter 102 comprises a drive cable or guidewire attached to the sensor 108 housed within a sheath. In some such configurations, the interface element 110 can act to translate or otherwise facilitate the translation of the drive cable and sensor 108 through the sheath while keeping the sheath substantially fixed in place.

In some examples, the processing engine 112 may be in communication with one or both of the sensor 108 and the interface element 110. For instance, in some examples, the interface element 110 is in communication with the processing engine 112 and provides an electromechanical interface to catheter 102. In some such examples, the interface element 110 facilitates communication between the processing engine 112 and the catheter 102 or elements thereof (e.g., sensor 108).

According to some examples, the processing engine 112 may comprise at least one programmable processor. In some examples, the processing engine 112 may comprise a computing machine including one or more processors configured to receive commands from a system user 116 and/or display data acquired from catheter 102 via a user interface 120. The computing machine may include computer peripherals (e.g., keyboard, mouse, electronic display) to receive inputs from the system user 116 and output system information and/or signals received from catheter 102 (e.g., rendered images, data curves, etc.). The user interface 120 may include a traditional PC or PC interface with software configured to communicate with the other components of the intravascular imaging system 100. In some embodiments, the user interface 120 may include a display 114 configured to display system information and/or representations of signals from the catheter 102 (e.g., intravascular images, pressure curves, etc.). In some embodiments, the user interface 120 includes a touchscreen display, which can act to both receive commands from a system user 116 and display intravascular imaging data from the catheter 102. In some examples, processing engine 112 may include memory modules for storing instructions, or software, executable by the one or more processors.

Figure 2:
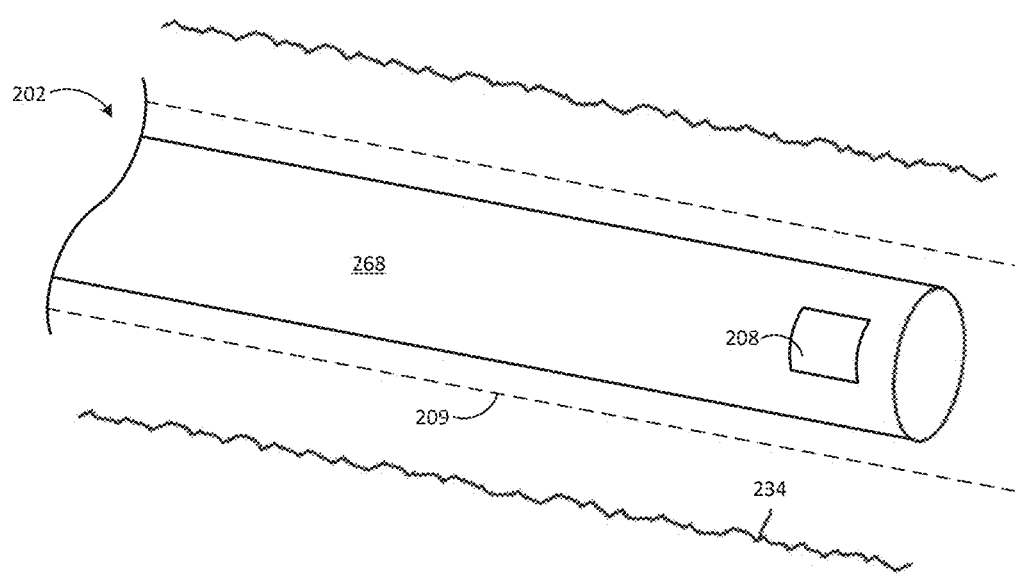
FIG. 2 is a diagram of the distal end of an exemplary catheter used in an exemplary IVUS system.

FIG. 2 is a diagram of the distal end of an exemplary catheter used in an IVUS system. The catheter 202 of FIG. 2 may be similar to catheter 102 described above. In the illustrated embodiment, catheter 202 comprises an IVUS catheter. The IVUS catheter 202 includes a sensor 208 such as a transducer configured to emit and receive ultrasonic pulses to generate a signal indicative of the interior structure of a patient's blood vessel 234. In some examples, sensor 208 may include a single transducer element or an array of transducer elements configured to emit and receive ultrasonic pulses. As shown, sensor 208 is coupled to drive cable 268, which may rotate and/or move the transducer distally or proximally within the patient's blood vessel 234. In some examples, the catheter 202 includes a sheath 209, which may remain stationary within the patient's blood vessel 234 while the drive cable 268 moves the sensor 208 distally or proximally within the sheath 209 and blood vessel 234.

Figure 3:
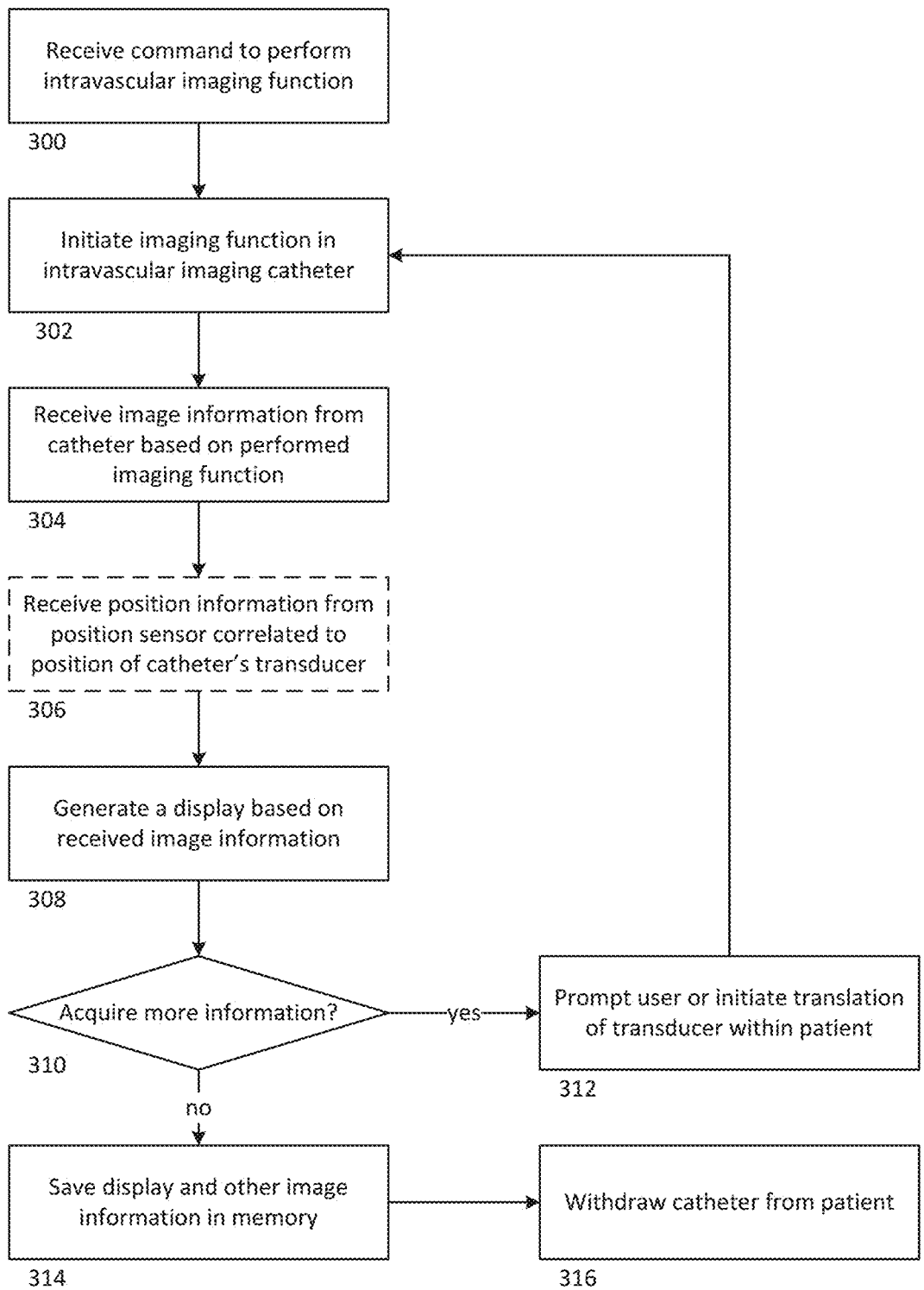
FIG. 3 is a step-flow diagram outlining a method in which one or more IVUS displays can be generated.

FIG. 3 is a step-flow diagram outlining a method in which one or more IVUS displays can be generated. After the catheter is inserted into a patient by a system operator, a processing engine such as those described herein can receive a command to perform an intravascular imaging function in step 300. The command can include parameters and scheduling of the imaging function. A user may command the processing engine to perform the imaging function. The user can manually program the desired parameters for the imaging function.

In step 302, the processing engine can initiate an imaging function commanded in the intravascular imaging catheter. This can include interfacing with the catheter, sending control signals and/or power to the catheter, rotating the catheter and/or the transducer within the catheter, or any other initiation process for performing the imaging function. In some embodiments, any single or combination of initiation processes can be initiated manually via a user interface. For example, initiating the imaging function may include directing electrical signals to the transducer resulting in the emitting of ultrasonic signals from the IVUS transducer.

After initiating an imaging function (e.g., step 302), in step 304, the processing engine can receive image information from the catheter based on the performed imaging function. The image information can be in the form of electrical or other signals from the catheter and/or transducer. In step 308, the processing engine can generate a display based on the received information. The display can be presented on a display where it can be viewed by a system user. The generated display can include, for example, a longitudinal image comprising image information from a plurality of locations within the patient and/or a cross-sectional image corresponding to a single transducer location within a patient. In some systems, the generated display can be generated by the processing engine in real-time and shown on the display as a live image. In some embodiments, the generated display can comprise a single snapshot of a cross section of a patient's vasculature triggered by a user, in which image information is captured for a single transducer location at a single time. In some embodiments, various generated displays are possible. In some systems, a user can select which mode of display is used (e.g., real-time, snapshot, etc.).

In step 310, the processing engine, based on received commands (e.g., step 300) and memory, can determine if more information is to be acquired. In some embodiments, the user can decide whether more information will be acquired. If so, the processing engine can initiate translation of the transducer within the patient, as in step 312. For example, in some systems, a selected mode of display, such as real-time display or a snap-shot display, can be used in step 310 to determine if more information is to be acquired.

In some embodiments, the intravascular imaging system comprises a translation mechanism. The translation mechanism can be configured for automated translation via a motor and/or manual operation. In some such embodiments, in step 312, the processing engine can interface with the translation mechanism and initiate translation directly via the motor. Some embodiments of the intravascular imaging system are configured for manual translation of the transducer. In such embodiments, the processing engine can prompt the user to translate the transducer.

After the transducer has been translated, step 302 may be repeated and an imaging function can again be initiated. The process may be repeated so that additional image information may be acquired at a different position within the patient. Once it is determined in step 310 that no additional information is to be acquired, the generated display or other associated image information can be saved in memory in step 314. In some embodiments, the user can manually save information to memory. Additionally or alternatively, the system may automatically save one or more pieces of information associated with system operation. If all operations utilizing the catheter are complete, in various embodiments the catheter can be withdrawn from the patient either manually or automatically in step 316.

As described, in some examples, the transducer is moved within the patient for acquisition of image data from a plurality of positions within the patient. In some embodiments, the transducer may be repositioned manually, or with the assistance of a translation mechanism. In some example, such a translation mechanism may assist a user in manually moving the transducer in any one of a desired distance, in a desired direction, and at a desired speed. Additionally or alternatively, a translation mechanism may include a motor capable of driving moving the transducer within the patient. The motor may be controlled manually or automatically, such as according to program instructions from the processing engine. Exemplary translation mechanisms are described further in U.S. patent application Ser. No. 13/894,045, filed May 14, 2013, and entitled "System and method for monitoring device engagement," which is assigned to assignee of the present application and is hereby incorporated by reference herein in its entirety.

In some embodiments in which the transducer is moved to a different position for the acquisition of additional image information, the processing engine can additionally receive position information from a position sensor as in step 306. Position information may be displayed and/or saved to memory with associated image information. In various examples, receiving image information such as in step 304 and receiving position information such as in step 306 can involve receiving any number of sets of image and position information from any number of distinct positions of the movable element of the position sensor. In some embodiments, receiving image information such as in step 304 and receiving position information such as in step 306 can include receiving a first set of image and position information corresponding to a first position of the transducer and a second set of image and position information corresponding to a second position of the transducer, such that the first and second positions are distinct from one another.

In some examples, the position information can be generated by a position sensor. Exemplary position information may comprise information regarding the relative position of a reference element of a position sensor and a movable element of the position sensor. In some configurations, the position of one of the reference and movable elements of the position sensor corresponds to the position of the transducer. Thus, relative motion of elements of the position sensor which can correspond to the relative motion of the transducer within the patient.

Because, in some embodiments, the position of the movable element of the position sensor is correlated to the position of the transducer in the patient's vasculature, the received sets of image and position information can correspond to distinct locations of the transducer. In some embodiments, at any one of the movable element positions for which the image and position information are received, the image and position information can be associated with one another as having been received at a common transducer position. Each set of image information can correspond to image information generated from a unique location within the patient's vasculature. The sets of position information can provide details on the spatial relationships between the unique locations. This can allow for the combination of image and position information from multiple movable element positions and the construction of a combined image.

In some embodiments, image and position information are received from a series of transducer positions by way of performing a pullback operation (e.g., all the way across a region of interest in a patient's blood vessel). Pullback can comprise inserting a catheter into a patient's vasculature and performing an imaging function while retracting the transducer through the patient, thereby acquiring image and position information corresponding to a plurality of transducer positions. Pullback can be executed by a motor, and can be initiated by a user via the user interface of the intravascular processing engine. A predetermined pullback operation can be performed, wherein the motor pulls the transducer back in a predetermined manner. In some embodiments, a user can manually control the operation of the motor and control the pullback operation. Motor controlled pullback can be automatically performed as part of an imaging schedule stored in memory. Automated pullback can include a feedback element configured to provide position information from the position sensor to the intravascular processing engine, and the intravascular processing engine can control the motor based on the position information. In some configurations, pullback can be performed entirely manually, in which a user manually translates the transducer within the patient while performing an imaging function. The execution of a pullback imaging operation can result in a plurality of sets of position and corresponding image information in which the relative spatial relationship between the sets of position information is known.

Image and position information from multiple movable element locations (associated with multiple transducer locations) can be combined to produce a three-dimensional volume of image information. When the relative transducer locations for each set of position and image information received are known, each set of image information can be arranged in a correct sequence and with appropriate spatial separation. In some embodiments, a single set of image data received by the intravascular processing engine comprises a cross-sectional image of the patient's vasculature proximate the transducer. A single set of position information can include a relative longitudinal location of the transducer within the patient's vasculature. A second set of image and position information received from a second position can comprise a second cross-sectional image, and the relative longitudinal location of the transducer when the image was taken. The relative relationship between the first and second transducer location can be determined by the first and second set of position information. Accordingly, the first and second set of image information can represent cross-sectional images taken at longitudinal locations a known distance apart. The cross sections can be combined along a longitudinal axis and appropriately spaced to form a three-dimensional representation of the two sets of information.

Figure 4:
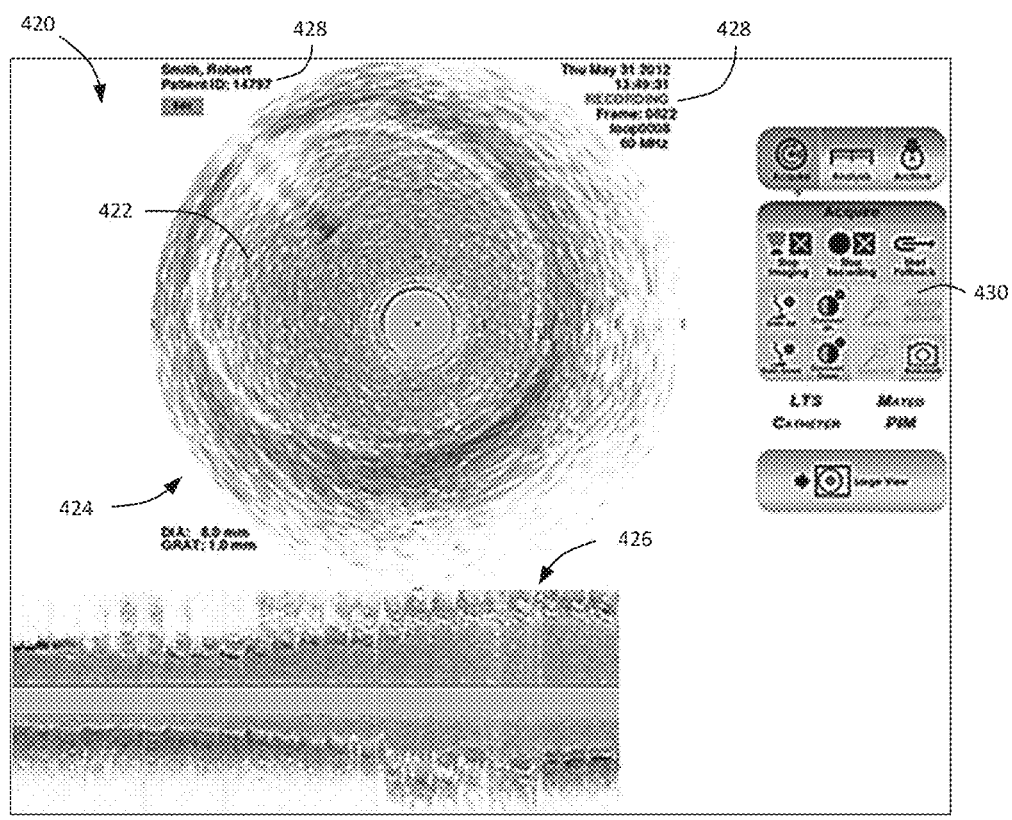
FIG. 4 shows an exemplary longitudinal image as can be constructed by an embodiment of an intravascular imaging system.

In general, any number of sets of image and position information (i.e., unique cross-sections) can be combined in this way to build up a three dimensional representation of the surroundings of the transducer, such as a patient's vasculature. Such a representation can be referred to as a longitudinal image. FIG. 4 shows an exemplary longitudinal image as can be constructed by an embodiment of an intravascular imaging system. FIG. 4 shows a display 420 such as might be shown on the display 114 of FIG. 1, for example. Referring again to FIG. 4, display 420 can include a cross-sectional image 424 configured to display a set of image information 422 corresponding to a particular transducer location. The display 420 can include a longitudinal image 426 configured to show a longitudinally arranges series of sets of image information, each from a particular transducer (e.g., sensor 108) location and arranged according to the associated position information. A longitudinal image 426 can be such that the longitudinal axis represents the direction of translation of the transducer in a patient's body. Accordingly, each data point along horizontal axis of a longitudinal image 426 can have associated therewith a corresponding cross-sectional image 424. While FIG. 4 shows the axis representing transducer motion being the horizontal axis, it will be appreciated that such characteristics could alternatively describe a vertical axis, or any other orientation, and in some embodiments can generally be a longitudinal axis. In some embodiments, the longitudinal image 426 is essentially a side-view of a plurality of cross-sectional images stacked on one another and arranged according to their relative positions. In some embodiments, each of the cross-sectional images can include a small amount of longitudinal information, which can be used to fill in gaps between transducer positions from which image information was received.

The display 420 as shown in FIG. 4 can include image data 428. Image data 428 can include various pieces of information about the cross-sectional image 424, the longitudinal image 426, the patient being imaged, other system information, etc. In some examples, image data 428 can include the patient name, a patient ID number, the time and date, frame number, and/or image information acquisition parameters such as an imaging frequency. In various embodiments, image data 428 can be displayed collectively in a single location on the display 420, or can be displayed across various locations. In the example of FIG. 4, image data 428 is located in multiple locations. In some embodiments, the display 420 can include a real-time display while continually performing one or more imaging functions. The display 420 can include a user interface 430 to provide command and control functionality to the user.

In some embodiments, the display 420 shown in FIG. 4 is part of the intravascular processing engine. The display 420 can comprise a touch screen for user input and manipulation. In some embodiments, the user can perform various functions with regard to the generated display 420. In some examples, the user can manipulate the brightness and/or contrast of the display 420, save a screenshot to memory, initiate an imaging function such as a pullback operation, terminate an imaging function, and so on. In the case of a longitudinal image 426, in some embodiments, a user can select a point along the longitudinal axis in the longitudinal image 426 for which to display the associated cross-sectional image 424 of the corresponding transducer position.

Exemplary intravascular systems and methods including position sensors are described in U.S. patent application Ser. No. 14/143,801, filed Dec. 30, 2013, and entitled "Position sensing in intravascular imaging," which is assigned to assignee of the present application and is hereby incorporated by reference herein in its entirety.

Figure 5A:
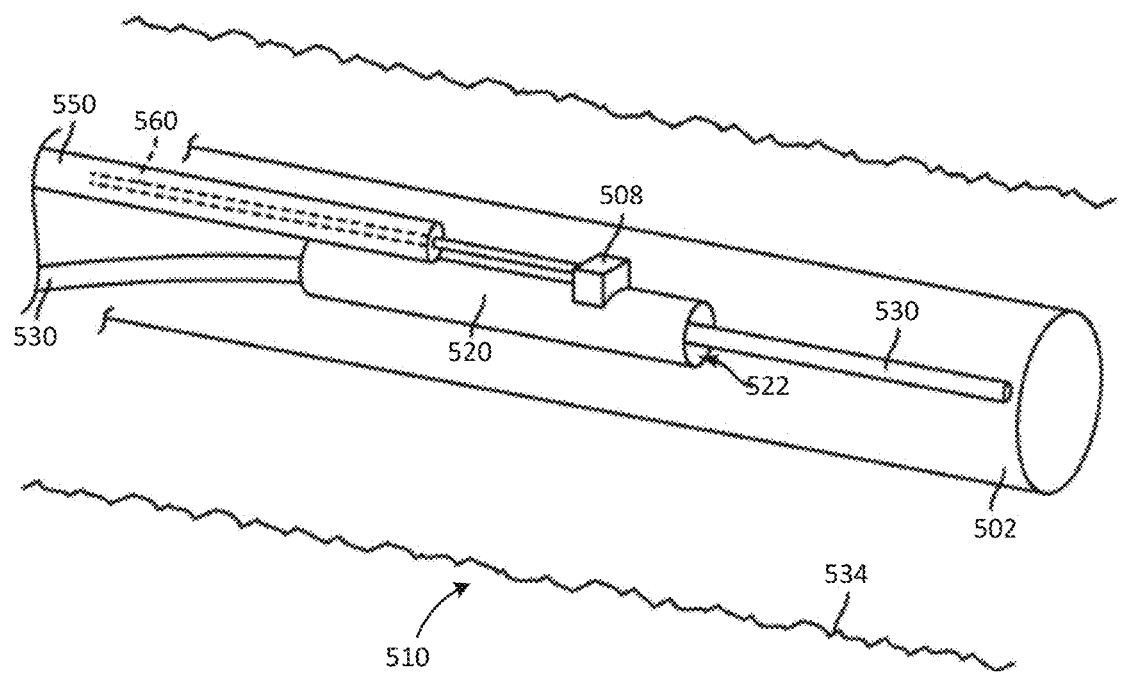
FIGS. 5A and 5B are perspective views of a sensor delivery device for measuring a physiological parameter in a patient.

Other exemplary systems such as 100 shown in FIG. 1 may include MPS systems. FIG. 5A is an exemplary MPS system including a sensor delivery device 510. The MPS system of FIG. 5A includes a distal sleeve 520 having a guidewire lumen 522 for slidably receiving a medical guidewire 530. A sensor 508 is coupled to the distal sleeve 520, sensor 508 being capable of sensing and/or measuring a physiological parameter of a patient and generating a signal representative of the physiological parameter. Thus, the distal sleeve 520, and hence, the sensor 508, may be positioned within a patient (e.g., within an anatomical structure of a patient, such as within a vein, artery, or other blood vessel, or across a heart valve, for example) by causing the distal sleeve 520 to slide over the medical guidewire 530 to the desired position.

The sensor delivery device 510 of FIG. 5A also includes a proximal portion 550, which is coupled to the distal sleeve 520. The proximal portion 550 includes a communication channel 560 for communicating the signal from the sensor 508 to a location outside of the patient (e.g., to processing engine 112 or display 114 of FIG. 1, or other computer, monitor, or another medical device). Communication channel 560 may comprise a fiber optic communication channel in certain preferred embodiments, such as where the sensor 508 is a fiber optic pressure sensor. Alternately, communication channel 560 may comprise an electrically conductive medium, such as one or more electrical conducting wires. Of course, many other forms of communication media may be suitable for transmitting the signal generated by sensor 508 to a location outside of the patient. In some embodiments of the invention, the communication channel 560 may comprise any of a variety of fluid and/or non-fluid communication media, such as a wireless communication link, or an infrared capability, or acoustic communications such as ultrasound, as possible examples.

During operation of the exemplary MPS system, the proximal portion 550 is also adapted to assist an operator (e.g., a physician or other medical staff) in positioning the distal sleeve 520 and the sensor 508 within an anatomical (e.g., vascular) structure of the patient. This is typically accomplished by an operator first inserting a "standard" medical guidewire 530 into a patient's vasculature and advancing it past an area of interest. The sensor delivery device 510 is then deployed by "threading" the distal sleeve 520 onto the guidewire 530 such that the lumen 522 slides over the guidewire 530, and advancing the distal sleeve 520 (and the associated sensor 508) by moving (e.g., pushing and/or pulling) the proximal portion 550 until sensor 508 is in the desired location.

The device 510 and the guidewire 530 are typically manipulated inside a guiding catheter 502, which has been placed in the anatomical (e.g., vascular) structure of interest. In certain preferred embodiments of the invention, the guidewire lumen 522 may be sized to slide over "standard" sized medical guidewires. For example, a number of manufacturers make medical guidewires that range in size from less than about 0.014 inches outer diameter to more than about 0.038 inches outer diameter, typically having a finite number of common sizes within this range. "Standard" size medical guidewires might, for example, have outer diameters of 0.010, 0.014, 0.018, 0.021, 0.025, 0.028, 0.032, 0.035, and 0.038 inches. Thus, in certain preferred embodiments of the invention, the guidewire lumen 522 may be sized appropriately to slide over a particular standard size medical guidewire. A device according to preferred embodiments of the invention may therefore be made available in a range of sizes corresponding to standard medical guidewire sizes.

One potential advantage of a sensor delivery device 510 according to embodiments of the invention is that it allows a physician to use the guidewire of their choice. Sensor delivery device 510 can be sized to be used with any guidewire. The physician may, for example, choose a particular guidewire based on its unique flexing and torque characteristics for certain procedures. Delivery device 510 according to various embodiments of the invention provides the physician with the ability to use whichever guidewire is deemed best suited for the particular application.

Another potential advantage of the sensor delivery device 510 is that it does not require repositioning of the guidewire in order to make sensor readings. Once the guidewire has been positioned across a stenotic lesion, for example, the sensor delivery device 510 can be positioned (e.g., advanced and/or retracted) over the guidewire and the sensor 508 can therefore be advanced and retracted across lesions to make pressure readings, for example, without moving the guidewire. A physician may also save time by not having to reposition the guidewire across the lesion or lesions to make such measurements.

In the example shown in FIG. 5A, the device 510 is being deployed using guiding catheter 502, which has been placed within a vascular structure of interest (in this example, blood vessel 534, which can be, for example, a coronary artery of the patient). In certain embodiments of the invention, the size or "footprint" (e.g., the width and/or the cross-sectional area) of device 510 may allow it to fit within certain standard sized guiding catheters. For example, in certain diagnostic applications, it would be desirable to have device 510 deployed within a certain sized guiding catheter (e.g., smaller than about 5 or 5 French (FR)).

In certain embodiments of the invention, the distal sleeve 520 of the device may be substantially concentric with the guidewire 530. The coupling of the proximal portion 550 to the distal sleeve 520 allows the guidewire 530 to separate from the rest of device 510 (e.g., in what is sometimes referred to as a "monorail" catheter configuration); this would typically occur inside the guiding catheter 502. The guidewire 530 and device 510 would both exit the patient at the proximal end of the guiding catheter 502 as separate devices. Having the device 510 and guidewire 530 separate allows the physician to independently control device 510 and guidewire 530, as necessary. It may also allow a physician to use a shorter guidewire for catheter exchange. For example, a monorail-type configuration may allow for the use of a guidewire that is approximately 170 to 200 cm long, whereas an "over-the-wire" configuration might require the use of a much longer (e.g., up to 500 cm or more) guidewire. Having the device 510 and guidewire 530 separate (except at the distal sleeve 520) may also result in less friction (e.g., within the guiding catheter 502) than if the device 510 and guidewire 530 had to be moved together as a unit. In some embodiments, a hydrophilic coating may be applied to various portions of the device to further reduce the amount of friction encountered, for example, when advancing or retracting device 510.

One diagnostic application in which various embodiments of the invention may be well-suited is the measurement of Fractional Flow Reserve (FFR). As noted above, the FFR measurement quantifies the degree to which a stenotic lesion, for example, obstructs flow through a blood vessel. To calculate the FFR for a given stenosis, two blood pressure measurements are needed: one pressure reading is taken on the distal side of the stenosis (downstream side), the other pressure reading is taken on the proximal side of the stenosis (upstream side). The FFR is therefore a unitless ratio of the distal pressure to the proximal pressure. The pressure gradient across a stenotic lesion is an indicator of the severity of the stenosis. The more restrictive the stenosis is, the more the pressure drop, and the lower the FFR.

Figure 5B:
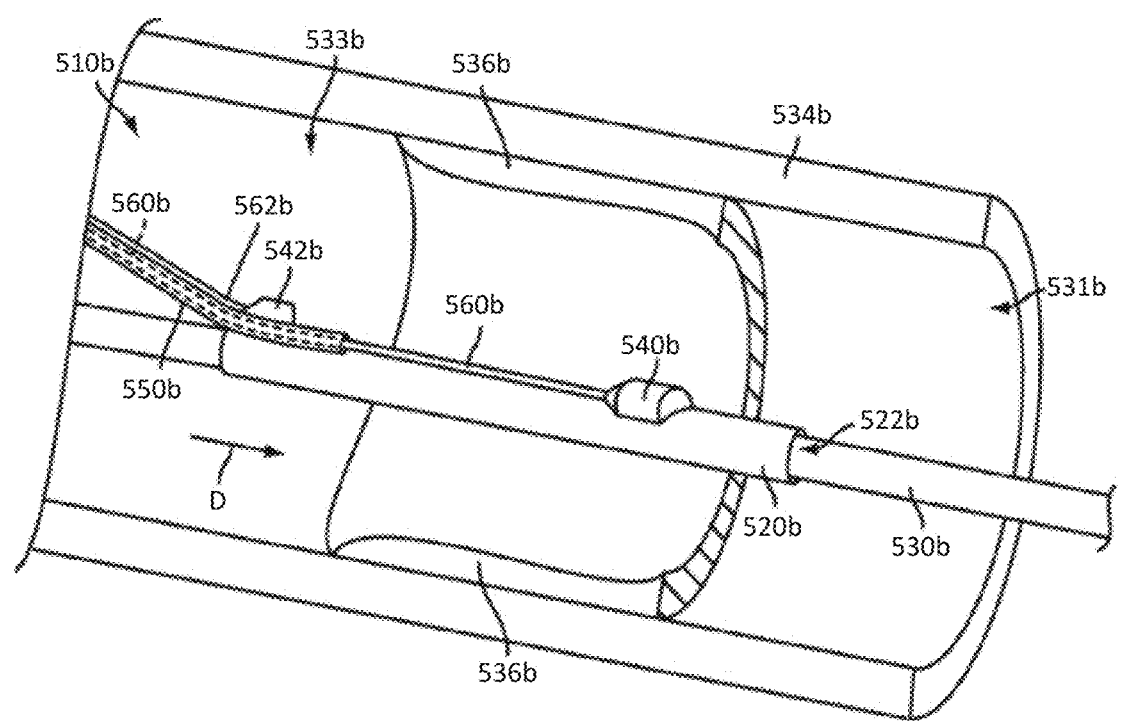

FIG. 5B is a perspective view of a sensor delivery device for measuring a physiological parameter in a patient according to an embodiment of the invention. The embodiment shown in FIG. 5B might, for example, be deployed to make an FFR measurement in a blood vessel of a patient. FIG. 5B shows a sensor delivery device 510b being deployed in a blood vessel of a patient (e.g., coronary artery 534b) across a stenosis (e.g., stenotic lesion 536b). To make an FFR measurement, for example, first sensor 540b may be positioned to measure distal (downstream) blood pressure, $P_d$, at a location 531b downstream of a location of interest (e.g., stenotic lesion 536b). First sensor 540b may then be positioned to measure proximal (upstream) blood pressure, $P_p$, at a location 533b upstream of a location of interest (e.g., stenotic lesion 536b). FFR is simply calculated as the ratio of distal pressure to proximal pressure, or $FFR=(P_d/P_p)$. The use of the terms "downstream" and "upstream" are with respect to the normal direction of blood flow, "D," as shown in FIG. 5B.

Sensory delivery device 510b of FIG. 5B includes a distal sleeve 520b having a guidewire lumen 522b for slidably receiving a medical guidewire 530b. In FIG. 5B, first sensor 540b is coupled to distal sleeve 520b. In the embodiment shown in FIG. 5B, first sensor 540b is coupled to an outer surface of distal sleeve 520b. The first sensor 540b is adapted to measure a physiological parameter of a patient, such as a blood parameter (e.g., blood pressure, temperature, pH, blood oxygen saturation levels, etc.), and generate a signal representative of the physiological parameter. In certain preferred embodiments of the invention, the first sensor 540b is a fiber optic pressure sensor adapted to measure blood pressure. An example of a fiber optic pressure sensor is a Fabry-Perot fiber optic pressure sensor, which is a commercially available sensor. Examples of Fabry-Perot fiber optic sensors are the "OPP-M" MEMS-based fiber optic pressure sensor (400 micron size) manufactured by Opsens (Quebec, Canada), and the "FOP-MIV" sensor (515 micron size) manufactured by Fiso Technologies, Inc. (Quebec, Canada). In certain alternate embodiments, first sensor 540b may be a piezo-resistive pressure sensor (e.g., a MEMS piezo-resistive pressure sensor), and in other embodiments, first sensor 540b may be a capacitive pressure sensor (e.g., a MEMS capacitive pressure sensor). A pressure sensing range from about −50 mm Hg to about +300 mm Hg (relative to atmospheric pressure) is desired for making most physiological measurements with sensor 540b, for example.

In embodiments of the invention using the Fabry-Perot fiber optic pressure sensor as the sensor 540b, such a sensor works by having a reflective diaphragm that varies a cavity length measurement according to the pressure against the diaphragm. Coherent light from a light source travels down the fiber and crosses a small cavity at the sensor end. The reflective diaphragm reflects a portion of the light signal back into the fiber. The reflected light travels back through the fiber to a detector at the light source end of the fiber. The two light waves, the source light and reflected light travel in opposite directions and interfere with each other. The amount of interference will vary depending on the cavity length. The cavity length will change as the diaphragm deflects under pressure. The amount of interference is registered by a fringe pattern detector.

FIG. 5B shows proximal portion 550b coupled to the distal sleeve 520b. The proximal portion 550b includes a communication channel 560b for communicating the physiological signal from the sensor 540b to a location outside of the patient (e.g., to a processor, display, computer, monitor, or to another medical device). The proximal portion 550b may preferably be formed of a material of sufficient stiffness in order to assist an operator (e.g., a physician or other medical staff) in positioning the distal sleeve 520b and the sensor 540b within an anatomical (e.g., vascular) structure of the patient.

One suitable material for the proximal portion 550b may be a stainless steel hypotube, for example. Depending on the application, the proximal portion 550b (sometimes also referred to as the "delivery tube") should typically be stiffer and more rigid than the distal sleeve 520b in order to provide a reasonable amount of control to push, pull and otherwise maneuver the device to a physiological location of interest within the patient. In interventional cardiology procedures, for example, at least a portion of the proximal portion 550b will be maneuvered within a guiding catheter positioned within the aortic artery. The proximal portion 550b in such an application should therefore be flexible enough to accommodate the arch of the aorta, while being rigid enough to push and pull the device. Accordingly, suitable materials for proximal portion 550b may also include (in addition to the aforementioned stainless steel hypotube) materials such as nitinol, nylon, and plastic, for example, or composites of multiple materials.

The communication channel 560b may be disposed along an outer surface of proximal portion 550b, or may be formed within the proximal portion 550b, as shown in FIG. 5B. For example, communication channel 560b may comprise a communication lumen that extends longitudinally through proximal portion 550b in some embodiments. Communication channel 560b may comprise a fiber optic communication channel in certain embodiments, such as where the sensor 540b is a fiber optic pressure sensor. Alternately, communication channel 560b may comprise an electrically conductive medium, such as electrical conducting wires, or other communication media suitable for transmitting the signal generated by sensor 540b. In preferred embodiments of the invention, the communication channel 560b comprises a non-fluid communication medium. In the embodiment shown in FIG. 5B, communication channel 560b (e.g., a fiber optic cable) extends distally beyond proximal portion 550b and is coupled to sensor 540b. The communication channel 560b in such an embodiment is at least partially housed within a communication lumen of the proximal portion 550b (e.g., a stainless steel hypotube).

FIG. 5B also shows an optional embodiment of the invention in which a second sensor 542b may be coupled to the device 510b. For example, a second sensor 542b may be coupled to proximal portion 550b such that the first and second sensor 540b, 542b are spaced apart sufficiently (e.g., a fixed distance apart) to span a stenotic lesion. This embodiment may offer the ability to measure FFR without having to reposition device 510b, since first sensor 540b can be placed distal of the stenotic lesion 536b to measure $P_d$, and second sensor 542b can be placed proximal of the stenotic lesion 536b to measure $P_p$. Second sensor 542b may have a communication channel 562b, which can be housed within proximal portion 550b, or can be disposed along an outside surface of proximal portion 550b, as shown in FIG. 5B, for example. Further, the ability to measure $P_d$ and $P_p$ substantially simultaneously may improve accuracy and/or reduce the effects of certain types of errors illustrated and described in U.S. Pat. No. 8,298,156, filed Sep. 11, 2009, and entitled "Physiological sensor delivery device and method," which is assigned to assignee of the present application and is hereby incorporated by reference herein in its entirety.

It should be noted that certain embodiments can have more than two sensors, and that the spacing between adjacent sensors in such embodiments may be varied to provide a variable spacing capability. In certain alternate embodiments of the invention, one or more sensors can be disposed on the proximal portion 550b with no sensors disposed on the distal sleeve 520b, for example. In some alternate embodiments, it may be desirable to have a plurality of sensors (two, or three, or four, or more sensors) spaced at known, fixed distances, disposed along the proximal portion 550b. This can, for example, provide the ability to measure $P_d$ and $P_p$ substantially simultaneously, regardless of lesion length, by selecting an appropriate pair of sensors (from among the plurality of sensors) placed across the lesion from which to obtain the $P_d$ and $P_p$ signals. Further, the sensors can have some form of radiopaque markings incorporated thereon (e.g., marker bands), which can provide a visual estimate of lesion size in conjunction with the measurement of physiological parameters (e.g., $P_d$ and $P_p$).

In various embodiments, device (e.g., 510, 510b) can fabricated from any suitable material, including those discussed above. In some examples, device (or a portion thereof) is fabricated from a magnetizable material. For example, one or more portions of the device, such as proximal portion (e.g., 250, 250b) and distal sleeve (e.g., 520, 520b), may be fabricated from magnetizable steel (e.g., cold worked stainless steel). Such a magnetizable material may be useful for developing a distance scale that can be assigned to a pressure gradient curve determined using the sensor carried by device and/or a sensor carried by the guidewire over which device translates.

It should be realized that there are other applications in which physiological parameter measurements can be facilitated with the devices and/or methods described herein. Other possible embodiments and implementations of various exemplary MPS systems are described in U.S. Pat. No. 8,298,156 (referenced above).

Figure 6:
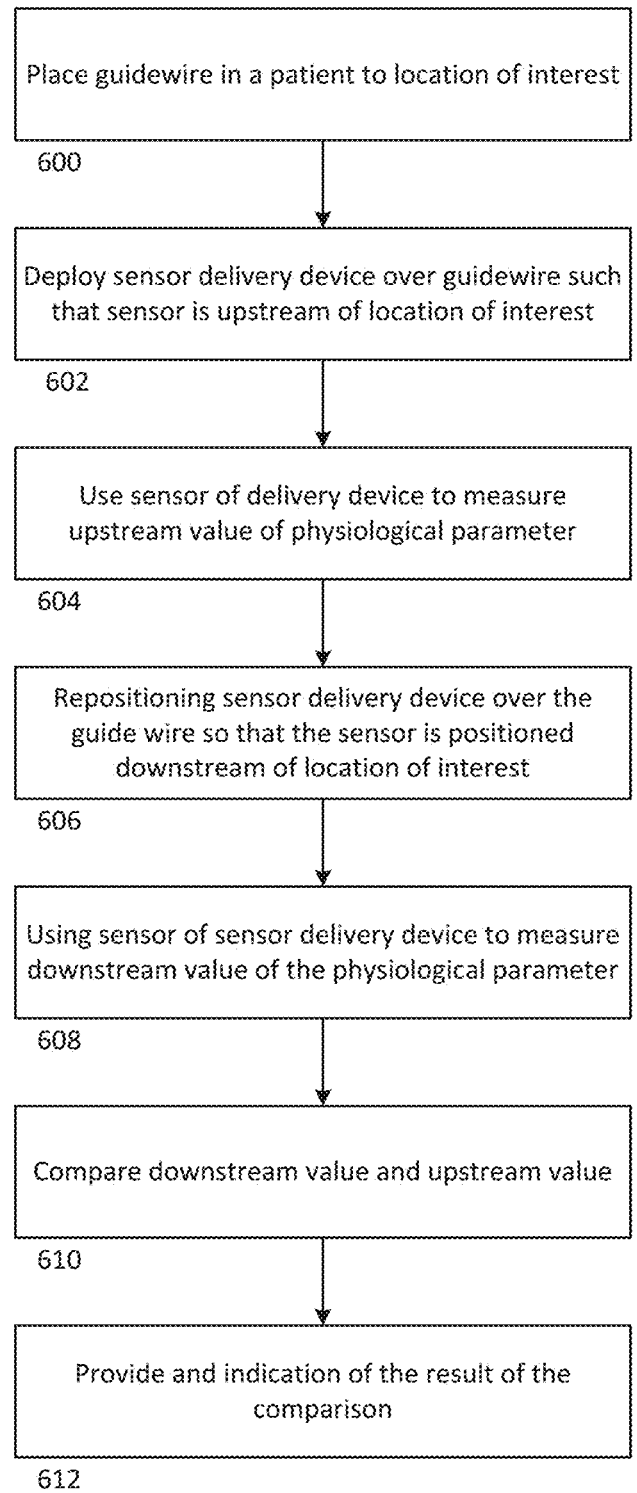
FIG. 6 is a process-flow diagram illustrating exemplary operation of an MPS system.

FIG. 6 is a process-flow diagram illustrating exemplary operation of an MPS system such as that shown in FIGS. 5A or 5B. The ordering of the actions shown in FIG. 6 is for exemplary purposes only. In some embodiments, a system such as a powered injection system or a diagnostic monitoring system may be capable of performing some of the steps of the method shown in FIG. 6 automatically, or alternately, after the operator has requested that the method be commenced through manual activation on the control panel (or secondary panel, if available).

Step 600 in FIG. 6 comprises placing a guidewire in a patient to a location of interest, such as a stenotic lesion, or across a heart valve, for example. In some embodiments, this may be a diagnostic guidewire, and a guiding catheter may also be inserted into the patient in conjunction with the guidewire. Step 602 comprises deploying a sensor delivery device over the guidewire such that the sensor is positioned upstream of the location of interest (e.g., upstream of a stenotic lesion, or on the high pressure side of a valve). In some embodiments, the sensor delivery device will have a sensor mounted to a distal sleeve that slides over the guidewire, and a proximal portion that is used by an operator to advance the distal sleeve over the guidewire to the desired location without having to move the guidewire. Step 604 comprises using the sensor of the sensor delivery device to measure a value of the physiological parameter upstream of the location of interest. In some embodiments, the physiological parameter is blood pressure, and the pressure measured by the sensor upstream of a stenotic lesion is the proximal pressure, $P_p$.

In some examples, the $P_p$ measurement such as that made in step 604 may be normalized to a measurement obtained from an independent source. "Normalizing" the $P_p$ measurement refers to the fact that an independent source (e.g., a fluid sensor for monitoring patient blood pressure during a procedure) will be used to obtain the $P_p$ value that will be used for later comparisons or calculations with the $P_d$ value (e.g., the downstream pressure) measured with the sensor of the sensor delivery device. The normalizing step basically ensures that the $P_p$ value measured with the sensor equals the $P_p$ value measured using the independent source so that no error is introduced (or that any error is minimized) when a subsequent downstream pressure measurement (e.g., $P_d$) is made. An adjustment, if needed, can be made to either $P_p$ value, although it may often be simpler to adjust the sensor-based $P_p$ value to match the independent source's $P_p$ value.

Step 606 comprises repositioning the sensor delivery device over the guidewire such that the sensor is downstream of the location of interest (e.g., downstream of the stenotic lesion). Step 608 comprises using the sensor of the sensor delivery device to measure a downstream value of the physiological parameter. In some embodiments, this step comprises measuring blood pressure downstream of the stenotic lesion, $P_d$. Step 610 comprises comparing the measured value downstream of the location of interest (e.g., $P_d$, downstream blood pressure) to a value measured upstream of the location of interest using the independent source (e.g., $P_p$). In some embodiments, the comparison made in step 610 may comprise calculating a ratio of the two measured values. In some embodiments of the invention, step 610 comprises calculating FFR as the ratio of downstream to upstream blood pressures, $P_d/P_p$. Step 612, which may be an optional step, comprises providing an indication of the result of the comparison made in step 610. For example, step 612 may comprise providing an indication of the calculated FFR value (e.g., numerical or graphical display or plot), and/or other cues may be provided to an operator. A color-coded indication of the severity of a stenotic lesion may be provided, for example, a RED indicator for FFR values less than 0.75, and/or a GREEN indicator for FFR values equal to or greater than 0.75. Other examples of indicators are possible, including non-visual indicators—an audible indication, an alarm sound for example, can alert an operator of an FFR value that is less than 0.75, which may prompt the operator to make a therapy decision.

As with the exemplary IVUS systems and methods described above, an MPS procedure may include acquiring position information associated with a position of the sensor within the patient. For example, position information may be indicative of the position of the sensor relative to the patient or the lesion within the patient, or may include relative position information indicative of the relative difference in position between the upstream and downstream measurements. In various examples, position sensors such as those described above with respect to IVUS systems may be used, for instance, including a movable element and a reference element. The movable element may be configured to move relative to the reference element as the sensor moves within the patient.

For patient with complex anatomical conditions, such as diffuse or long lesions, lesion severity may be measured by generating a pressure curve across the lesion. Thus, in some examples, quantifying lesion severity in a diffusely affected coronary vessel may require a pressure pull-back curve indicating the pressure gradients within the vessel. This can be done by taking simultaneous pressure readings while withdrawing the pressure sensor (e.g., MPS) from a distal to a proximal position, for instance, during a steady-state maximum adenosine hyperemia. The resulting pressure data can be used to generate a corresponding pressure curve that represents the pressure gradient over the entire length of the vessel. Such pressure curves may demonstrate the exact location and severity of the lesion. In some instances, this pull-back curve can be extremely useful in guiding spot-stenting in a vessel with long and diffuse lesions.

Figure 7:
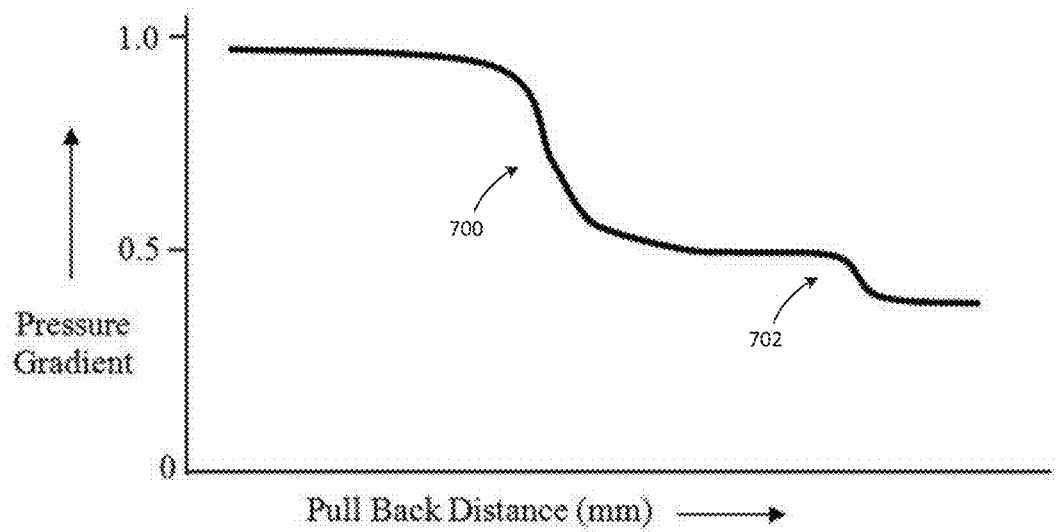
FIG. 7 is an exemplary plot showing a variety of pressure measurements associated with a variety of corresponding positions within a blood vessel of a patient.

Accordingly, in some examples, a plurality of measurements (e.g., pressure measurements, pressure gradients, etc.) may be acquired at a plurality of locations within the patient's vasculature. Such the relative positions at which such measurements are acquired may be determined, for example, using position information from the position sensor. The processing engine 112 may act to effectively combine measurement information and associated position information. The plurality of measurements may be displayed together with reference to the relative position at which each measurement was taken, such as on display 114. FIG. 7 is an exemplary plot showing a variety of pressure measurements associated with a variety of corresponding positions within a blood vessel of a patient.

Such data may be useful in identifying the positions of lesions or other pressure-affecting features within a blood vessel. For example, in some instances, severe gradients in pressure vs. position may be indicative of severe lesions within the vessel. In the illustrated example of FIG. 7, a first pressure gradient 700 may be indicative of a severe lesion in the vessel. A second, less severe gradient 702, may be indicative of a more minor lesion within the vessel. Accordingly, data such as that shown in FIG. 7 may be used to locate lesions within the patient's blood vessel. In some such embodiments, position information associated with the pressure data may be used to locate the location of the lesion in order to provide effective therapy at the lesion location. In some examples, the acquisition of pressure data over a distance such as shown in FIG. 7 may be useful for decision-making with regard to diagnosis and treatment of patients, such as those with complex coronary disease. The data may be particularly useful for determining which lesions within the patient should be treated and which need not be.

In some instances, pullback of the pressure sensor is done very slowly to capture pressure readings over the course of one or more heartbeats at each location. In some embodiments, to speed up the pullback, short interval instantaneous pressure measurements from multiple sensors can be recorded, such as sensors 540b and 542b of FIG. 5B. The multiple pressure recordings can be normalized to one of the readings to get a relative pressure gradient using a much shorter time interval at each measurement location.

Figure 8:
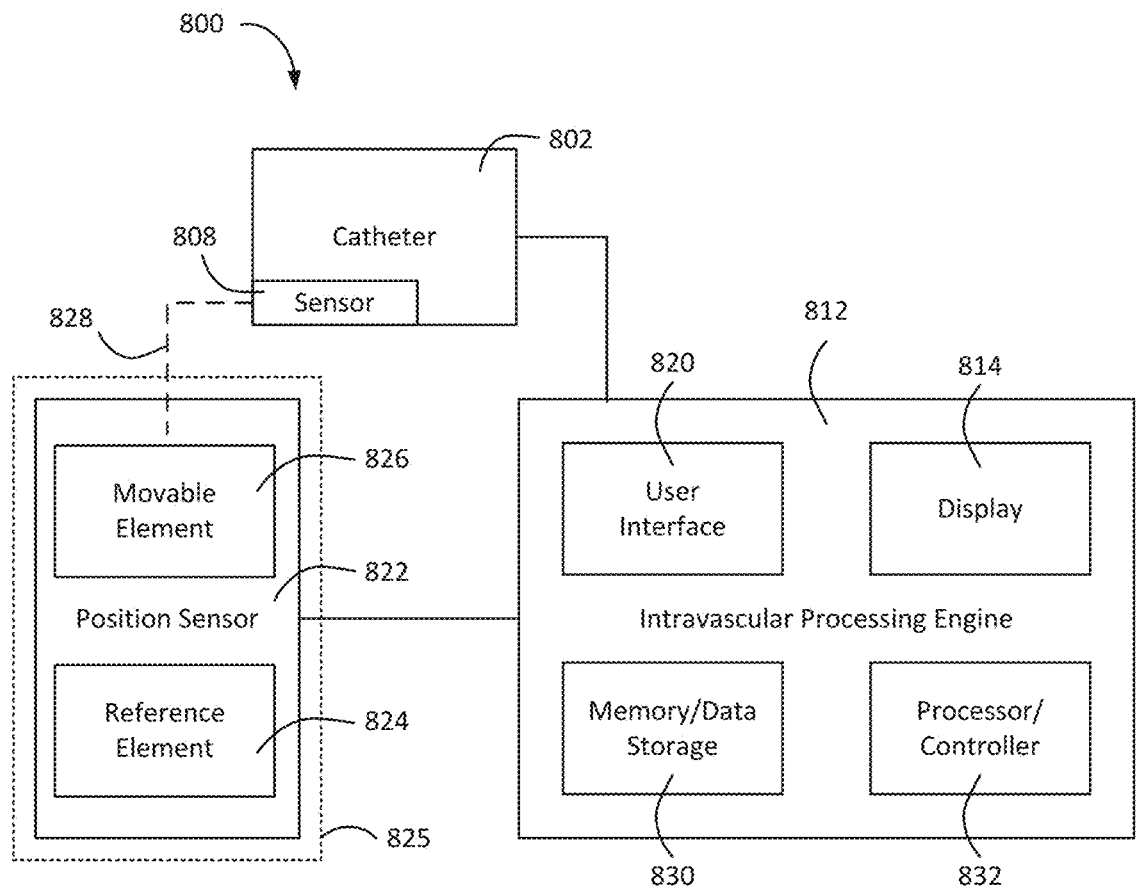
FIG. 8 is a system-level block diagram of an embodiment of an intravascular system that includes a position sensor.

As previously discussed, in many intravascular procedures, it can be advantageous to know at least relative position information regarding the location of various aspects of the system. FIG. 8 is a system-level block diagram of an embodiment of an intravascular system that includes a position sensor. In particular, the illustrative system 800 of FIG. 8 comprises a catheter 802, a position sensor 822 and a processing engine 812. The catheter 802 can include a sensor 808 and can be in communication with the processing engine 812. In some embodiments, the processing engine 812 is in direct communication with the sensor 808. In the embodiment of FIG. 8, the processing engine 812 comprises a display 814, a user interface 820, memory/data storage 830 and a processor/controller 832. These components may be integrated into, for example, a touch screen display and/or a computer.

In some embodiments, the catheter 802 or the sensor 808 within the catheter 802 can be translated within a patient's vasculature while performing a diagnostic or therapeutic function. In such cases, the processing engine 812 can receive information from the sensor 808 at a plurality of positions. In some embodiments, processing engine 812 can receive the information from a plurality of sensor positions and construct an aggregate data set. For example, in the case of an IVUS system, image data associated with a plurality of locations may be aggregated to construct a figure such as in FIG. 4. In the case of an MPS system, pressure or other data may be aggregated to generate a plot such as is shown in FIG. 7. Such aggregate data sets may be processed for presentation on a display 814 that comprises information from at least a subset of the plurality of sensor 808 positions. To construct such an aggregate set of information, it can be useful for the processing engine 812 to detect at least a relative relationship between the positions from which the information was received. Accordingly, some embodiments of the intravascular system 800 include a position sensor 822.

The position sensor 822 shown in FIG. 8 may include a movable element 826 and a reference element 824. The position sensor 822 can comprise, for example, a potentiometer, an encoder, a linear variable differential transformer, or other suitable position sensor. Such a position sensor 822 can be integrated into the intravascular system 800 and placed in communication with the processing engine 812. The movable element 826 of the position sensor 822 can have a movable element position that is correlated to the position of the sensor 808. The correlation between the sensor position and the position of the movable element 826 is represented by broken line 828 in FIG. 8. The reference element 824 of the position sensor 822 can be substantially fixed relative to motion of sensor 808 during a variety of intravascular processes (e.g., ultrasonic imaging, pressure sensing, etc.). In such embodiments, because of the correlation between the sensor position and the movable element position, the position sensor 822 can be configured to determine the relative motion of the sensor 808 with respect to the reference element 824 of the position sensor 822. In some embodiments, the position sensor 822 can determine the relative motion of the sensor 808 with respect to the reference element 824, which the position sensor 822 can communicate to other components of the processing engine 812.

As shown in FIG. 8, the position sensor 822 can be in communication with the processing engine 812. In some embodiments, the processing engine 812 can be configured to receive position information from the position sensor 822. Position information can comprise information regarding the position of the movable element 826 of the position sensor 822 relative to the reference element 824. The position information can include information received from an encoder, resistance information or other electrical data from a potentiometer, or any other signals or information from various kinds of position sensors. In embodiments in which the position sensor 822 determines the relative motion of the sensor 808 with respect to the reference element 824, the position sensor 822 can provide that position information to the processing engine 812. In some embodiments, the position sensor 822 can provide information regarding the movable element 826 and the reference element 824 to the processing engine 812, and the processing engine 812 can determine the relative motion of the sensor 808 with respect to the reference element 824. As discussed, the position of the movable element 826 can be correlated to the position of the sensor 808 of the catheter 802. In some embodiments, the position sensor 822 can compare the location of the movable element 826 with that of the reference element 824, account for how the location of the movable element 826 correlates to that of the sensor 808, and determine the location of the sensor 808 relative to that of the reference element 824. In such embodiments, the position sensor 822 can provide the location of the sensor 808 to the processing engine 812. In some embodiments, the position sensor 822 can simply send information concerning the location of the movable element 826 relative to that of the reference element 824 to the processing engine 812. In some such embodiments, the processing engine 812 can compare the location of the movable element 826 with that of the reference element 824, account for how the location of the movable element 826 correlates to that of the sensor 808, and determine the location of the sensor 808 relative to that of the reference element 824. In other embodiments, the processing engine 812 may measure the motion of the movable element 826 relative to the reference element 824 and determine the motion of the sensor therefrom.

In some embodiments, the processing engine 812 can be configured to receive both sensor information (e.g., image information from IVUS transducer, pressure information from a pressure sensor such as an MPS, etc.) from the intravascular catheter 802 and position information from the position sensor 822. The processing engine 812 can associate particular image information with a relative position of the sensor 808. The processing engine 812 can be configured to generate a display based on the sensor information and the position information.

The processing engine 812 can receive and process sensor information and position information corresponding to multiple longitudinal positions within the blood vessel being analyzed. In some configurations, the processing engine 812 can receive a first set of sensor information and a first set of position information, each corresponding to a first movable element position. The processing engine can additionally receive a second set of sensor information and a second set of position information, each corresponding to a second movable element position. In general, the sensor information and position information can comprise information corresponding to any number of movable element positions. In some preferred embodiments, the processing engine 812 can process sensor information and position information in real time for several locations during translation of the sensor to display real-time data regarding the blood vessel being analyzed.

As discussed elsewhere herein, in some embodiments the movable element position is correlated to the position of the sensor 808. Thus, first and second sets of sensor and position information corresponding to first and second movable element positions can also correspond to first and second sensor 808 positions. The sensor 808 can be translated within the patient's vasculature to various positions, while the movable element 826 can move relative to the reference element 824 correspondingly. The sensor 808 can be translated through the patient's vasculature in a number of ways. In some embodiments, the catheter 802 translates through the patient's vasculature. The sensor 808 can translate within the catheter 802, within a sheath, for example. In some embodiments, the intravascular imaging system can include a translation mechanism configured to translate the catheter 802 and/or the sensor 808 within the catheter 802.

In various embodiments, elements of the position sensor 822 may be positioned in various portions of a system. For instance, in some examples, one or both of the movable element 826 and the reference element 824 may be included on a translation mechanism. Additionally or alternatively, one or both of such elements may be disposed on or otherwise integrated into catheter 802. In some examples, the system 800 may include a dedicated position sensor assembly 825 for housing or otherwise supporting at least a portion of the position sensor 822.

In some embodiments, at least a portion of the catheter, such as a drive cable (e.g., 268) of an IVUS catheter or a proximal portion (e.g., 550, 550b) of an MPS catheter, is fabricated from a magnetizable material. In some embodiments, such a portion of the catheter is alternatingly magnetized and demagnetized. In other embodiments, a magnetizable portion of the catheter may include magnetic domains having varying magnetizations. For example, an alternating magnetic field may be induced on a magnetizable portion of the catheter at known intervals (e.g., every 1 millimeter). In various embodiments, the magnetization may be in an axial or a radial direction with respect to the catheter. The magnetizable portion of the catheter can then be passed through or otherwise near a magnetic pickup that counts magnetic field fluctuations (e.g., pulses) associated with the magnetizable portion of the device. In some examples, with reference to FIG. 8, the movable element (e.g. 826) of the position sensor (e.g., 822) may include the magnetizable portion of the catheter (e.g., including magnetic domains). Similarly, the reference element (e.g., 824) of the position sensor (e.g., 822) may include a pickup configured to detect magnetic domains of the catheter.

In some such embodiments, since each magnetic field fluctuation is correlated to a known distance (e.g., 1 mm), the pulses counted by the magnetic pickup device can provide a distance scale that is then associated with other processes performed by the catheter (e.g., IVUS imaging or MPS pressure sensing vis sensor 108). The magnetic pickup device may be in communication with control elements or circuitry. Such control elements or circuitry may be associated with the intravascular processing engine (e.g., 112). Accordingly, the sensor (e.g., 108) and magnetic pickup device may together provide sensor information and position information to the intravascular processing engine. As previously described, the intravascular processing engine may combine the sensor information and position information, for example, for generating a display (e.g., longitudinal IVUS image as in FIG. 4 or an MPS pressure curve as in FIG. 7).

Figure 9A:
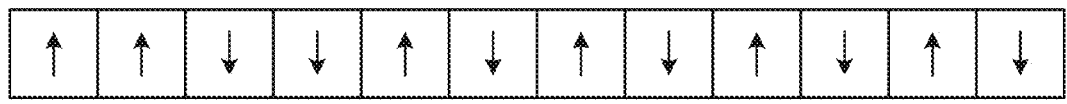
FIGS. 9A-9C illustrate exemplary magnetic domains of a magnetizable portion of a catheter.
Figure 9B:
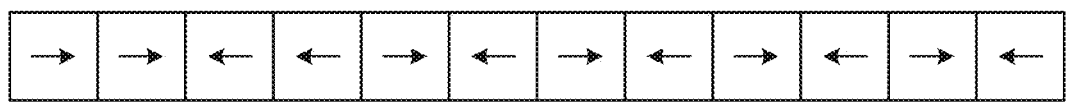
Figure 9C:
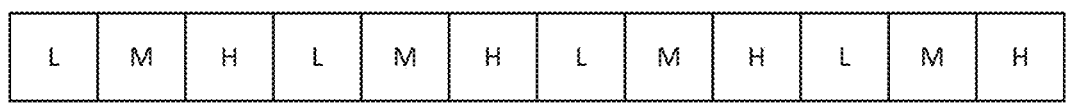

FIGS. 9A-9C illustrate exemplary magnetic domains of a magnetizable portion of a catheter. FIG. 9A shows a magnetizable portion of a catheter 902a having axially magnetized domains. As shown, a variety of magnetic domains have magnetization directions indicated by arrows pointing outward from the magnetizable portion of catheter 902a. In the illustrated embodiment, domains are 1 mm in length, though many domain sizes may be used. The order of domains by magnetization direction may be defined so as to detect not only distance of catheter travel, but also direction. Similar to the magnetizable portion of catheter 902a, magnetizable portion of catheter 902b of FIG. 9B includes a plurality of magnetic domains. Similarly, the directions of the magnetization of the domains are indicated by arrows. In contrast to the magnetizable portion of catheter 902a in FIG. 9A, the magnetization directions in the magnetizable portion of catheter 902b are aligned axially. As described above, order of domains by magnetization direction may be defined so as to detect not only distance of catheter travel, but also direction.

Additionally or alternatively to varying magnetization directions of magnetizable portions of catheters (e.g., 902a, 902b), in some examples, the magnitude of the magnetization of various domains may differ. FIG. 9C shows a magnetizable portion of a catheter 902c having domains of different magnetization magnitudes. In the illustrated embodiment, domains are configured to have magnetization magnitudes that are low (L), medium (M), or high (H) in value. Motion of the magnetizable portion of the catheter 902c may be detected based on detected changes in a magnetic field strength at a fixed location. In some examples, detecting changes in the magnetic field strength may provide an indication of the direction of movement of the magnetizable portion of the catheter 902c. For instance, with respect to the illustrated embodiment, a detected transition from L to H indicates motion in a first direction, while a detected transition from L to M indicates motion in a second direction, opposite the first. In various examples, magnetic domains in the magnetizable portion of the catheter 902c may have magnetization directions oriented radially or axially. In some embodiments, the magnetizations of each of the magnetic domains may be parallel to one another. In other examples, magnetization directions may alternate or be arranged in any other order. In some embodiments, detected magnetization directions may be used in conjunction with the detected magnitude of the magnetization to determine one or both of the amount and the direction of motion of the magnetizable portion of the catheter 902c.

As described, various portions of the catheter may include magnetically detectable domains. In some embodiments, movement of such portions of the catheter may be detected by one or more pickup proximate the location of the detectable magnetic domains during typical system operation. For example, in some embodiments, magnetic domains may be integrated into one or more system magnetizable portions of a catheter, such as a cable configured to move simultaneously with the intravascular sensor within the patient. Such a cable may refer to one or more elements of the system that move simultaneously with a sensor (e.g., 108 in FIG. 1) of the catheter. In some examples, the sensor may include an IVUS transducer or a pressure sensor (e.g., MPS) coupled to such a cable. For example, in some such systems, cable may include a drive cable (e.g., 268 of FIG. 2) of an IVUS system catheter or a proximal portion (e.g., 550) of a sensor delivery device (e.g., 510 of FIG. 5A) such as a hypotube in an MPS system. Other movable portions of the catheter or system may additionally or alternatively include such detectable magnetic domains. In various embodiments, one or both of magnetic domains and the magnetizable portion of the catheter (902*a-c*) configured to move during system operation may be considered to be a movable element (e.g., 826) of a position sensor (e.g. 822).

In some embodiments, the magnetization of magnetic domains may be a material property of the magnetizable portion of the catheter. That is, the portion of the catheter may be made from a magnetic materials (such as cold-worked stainless steel) into which magnetic domains have been "written" or otherwise formed. In some other examples, magnetizable portion of the catheter may be constructed from a non-magnetic material, but may include a magnetic coating applied thereto. The magnetic coating may similarly include magnetic domains that have been "written" thereto.

Figure 10:
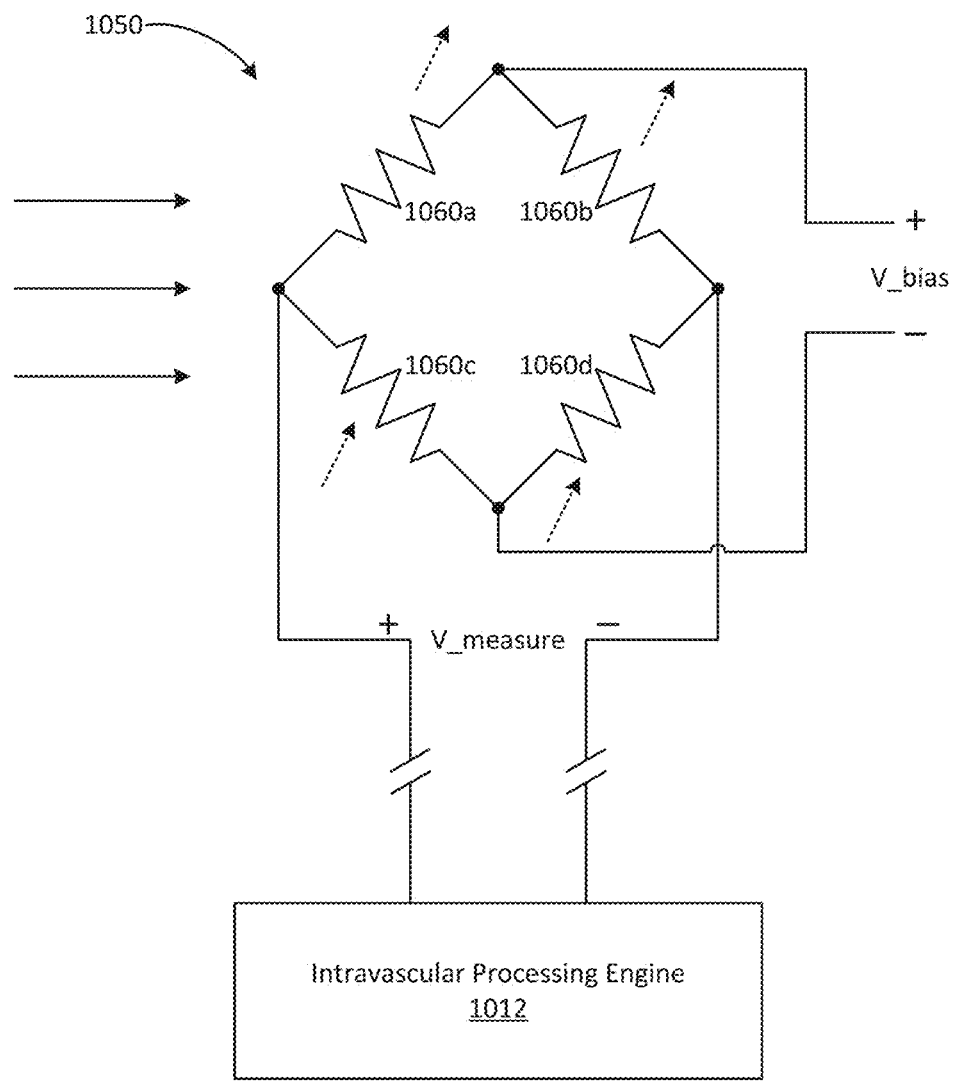
FIG. 10 is a schematic diagram of an exemplary magnetic pickup for use in an intravascular system.

FIG. 10 is a schematic diagram of an exemplary magnetic pickup for use in an intravascular system. The pickup 1050 of FIG. 10 includes a plurality of magneto-resistive devices 1060*a*-1060*d* arranged in series and forming a circuit. A bias voltage (V_bias) is applied across opposite sides of the network of devices 1060*a*-1060*d*, and an applied magnetic field (illustrated in broken lines) is applied across the network. In some examples, the magneto-resistive devices 1060*a*-1060*d* experience anisotropic magneto-resistance (AMR), in which the resistance of the device 1060*a*-1060*d* depends on the strength and direction of an experienced magnetic field. In the illustrated embodiment, a magnetic field, such as from the magnetic domains of the catheter (e.g., as shown in FIGS. 9A-9C; illustrated in solid lines), is experienced by the network of magneto-resistive devices 1060*a*-1060*d*. The combination of the applied and experienced magnetic fields ultimately affects the resistance of the magneto-resistive devices 1060*a*-1060*d*. The changes in resistance in turn affect the amount of the bias voltage dropped across each of the devices.

In the illustrated embodiment, a voltage (V_measure) is measured between the junction of magneto-resistive devices 1060*a* and 1060*c* and the junction of magneto-resistive devices 1060*b* and 1060*d*. Thus, the measured voltage (V_measure) is indicative of the difference in voltage dropped by magneto-resistive device 1060*a* and magneto-resistive device 1060*b*. As will be understood by those skilled in the art, the net magnetic field may differently affect the respective resistances of devices 1060*a-d* and 1060*b*. As a result, the presence and absence of a magnetic field (or the switching of direction of a magnetic field) will result in changes of relative resistances of devices 1060*a-d* and a change in the measured voltage (V_measure).

Accordingly, the measured voltage (V_measure) may be monitored to detect changes in the magnetic field at the pickup 1050. Thus, changes in the measured voltage may be used to indicate the movement of a magnetizable portion of the catheter past the pickup 1050. In the illustrated embodiment, the pickup 1050 is shown as being in communication with intravascular processing engine 1012. The intravascular processing engine 1012 may be configured to receive a signal indicative of the measured voltage (V_measure). In some examples, the intravascular processing engine 1012 may measure the voltage directly. Additionally or alternatively, the intravascular processing engine 1012 may be configured to apply the bias voltage (V_bias) to the pickup 1050.

In some alternative embodiments, one or both of supplying the bias voltage and measuring the measured voltage may be performed by one or more separate components. For instance, in some embodiments, the bias voltage may be provided by a standalone device such as a separate power supply, a battery, or the like. Additionally or alternatively, the measured voltage may be applied to additional circuitry separate from the intravascular processing engine 1012. Such additional circuitry may be configured to detect changes in the measured voltage and output a signal to the intravascular processing engine 1012 representative of such changes. For example, in some embodiments, additional circuitry configured to receive the measured voltage may communicate the measured voltage to the intravascular processing engine 1012. In other examples, the additional circuitry may determine when a change in the measured voltage occurs (e.g., crosses above or below a threshold, changes sign, etc.). The additional circuitry may communicate a signal to the intravascular processing engine 1012 indicative of the change, but need not include the value of the measured voltage.

In general, in various embodiments, additional circuitry may communicate a signal to the intravascular processing engine 1012 representative of the magnetic properties of the magnetizable portion of the catheter proximate the pickup 1050. The intravascular processing engine 1012 may receive such information and make subsequent determination of the relative position or motion of elements of the catheter within a patient. Communication between circuitry and the intravascular processing engine 1012 may be wired or wireless, for example via a Bluetooth or Wi-Fi connection. It will be appreciated that the connections between the pickup 1050 and the intravascular processing engine 1012 illustrate exemplary connections according to some embodiments. As described, the bias voltage may be applied by, controlled by, or entirely independent from operation of the intravascular processing engine 1012. Similarly, the measured voltage may be directly applied to the intravascular processing engine 1012 or communicated thereto by additional circuitry either wired or wirelessly. Additionally or alternatively, the additional circuitry may provide a signal based on the measured voltage without actually directly communicating the value of the measured voltage.

As previously mentioned, magnetic domains may be written into a cable (or other system component) having radially or axially oriented magnetizations. One or more pickups such as 1050 of FIG. 10 may be configured to produce outputs based on detected magnetic domains (and changes therein due to catheter movement) that are either radial or axial. In some embodiments, movement of such portions of the catheter may be detected by one or more pickup proximate the location of the detectable magnetic domains during typical system operation. Accordingly, in some examples, a pickup such as 1050 of FIG. 10 may be used as a reference element (e.g., 824) of a position sensor (e.g., 822) in an intravascular system.

Figure 11:
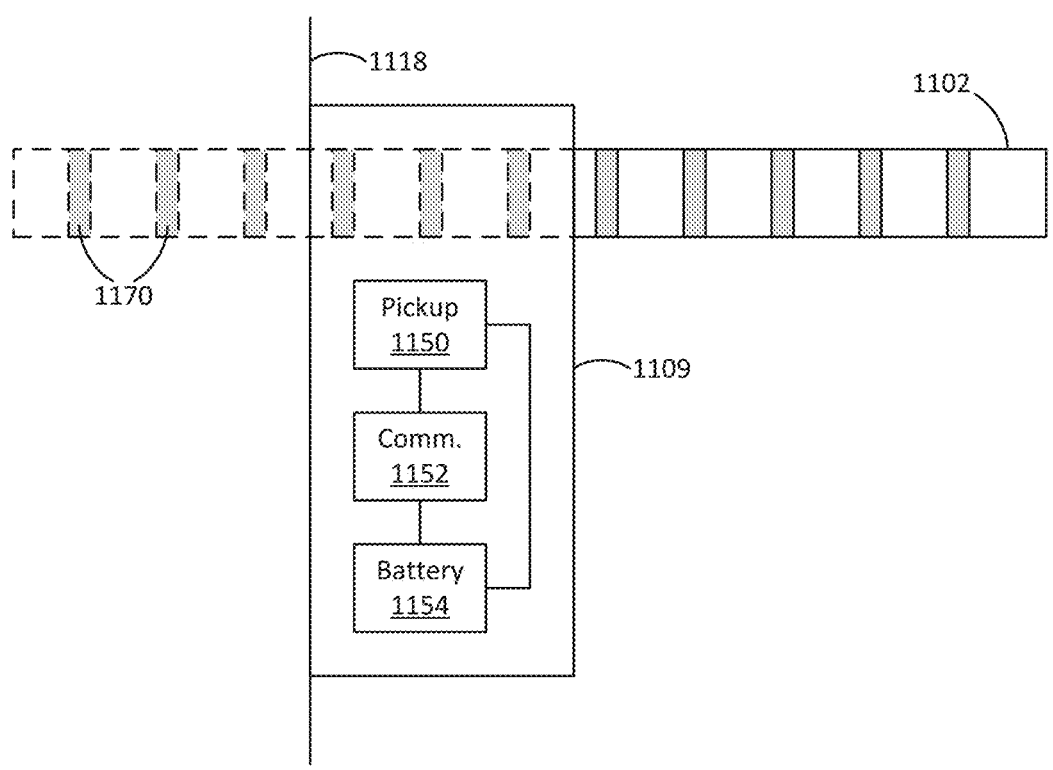
FIG. 11 is a schematic diagram showing a pickup located in a valve receiving the catheter.
Figure 12:
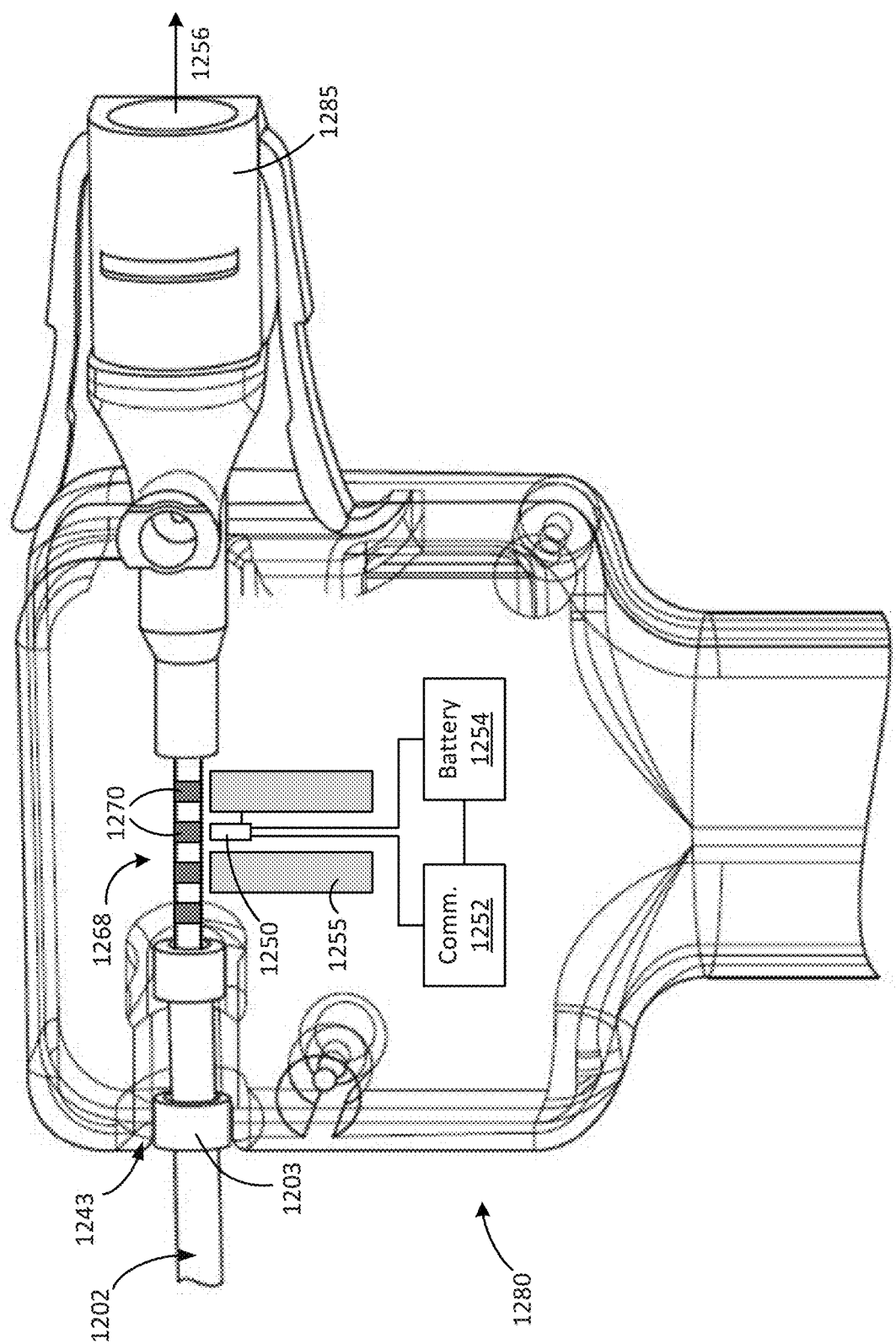
FIG. 12 is a cross-sectional view of an exemplary position sensing assembly.

FIGS. 11-13 are exemplary diagrams illustrating a variety of pickup locations according to various embodiments of the invention. FIG. 11 is a schematic diagram showing a pickup located in a valve receiving the catheter. As shown, the catheter 1102 extends through valve 1109 placed in the patient 1118. Valve 1109 may include, for example, a hemostasis valve as described above. In the illustrated embodiment, portions of the catheter 1102 shown in solid lines are outside of the patient 1118 and the valve 1109, while those in broken lines extend at least partially into the valve 1109.

The catheter 1102 includes magnetic domains 1170 positioned along the catheter 1102 proximate the valve 1109 during typical intravascular operations. In various embodiments, the magnetic domains 1170 may be a part of a movable portion of the catheter 1102, such as a drive cable in an IVUS system or a proximal portion of a sensor delivery device in an MPS system. As described elsewhere herein, magnetic domains 1170 may have magnetizations oriented in a variety of directions and/or having a variety of magnitudes. Such differences in magnetic domains 1170 allow for differentiation between proximate domains 1170 in order to detect movement of a portion of the catheter 1102.

The valve 1109 includes a pickup 1150 positioned proximate the catheter 1102 such that the pickup 1150 may be capable of detecting magnetic domains 1170 of the catheter 1102. The pickup 1150 may be a magnetoresistive sensor such as that illustrated in FIG. 10, or other pickup capable of detecting magnetic domains 1170, such as a Hall Effect sensor. Pickup 1150 may be configured to output a signal based on the magnetic field present at the pickup. The magnetic field at the pickup 1150 may be indicative of the magnetization of the magnetic domains 1170 proximate the pickup 1150. Accordingly, changes in the signal may be representative of changes in the magnetic domains 1170 proximate the pickup 1150, and thus changes in position of a portion of the catheter 1102.

In the illustrated embodiment, the valve 1109 includes a communication unit 1152 in communication with the pickup 1150. Communication unit 1152 may be configured to receive signals from the pickup 1150. For example, the communication unit 1152 may be configured to receive a measured voltage (V_measure) from a pickup such as illustrated in FIG. 10. Communication unit 1152 may be further configured to communicate the signals or representative signals elsewhere in the system. The communication unit 1152 may be capable of communicating signals by one or both of wired or wireless transmission. In some embodiments, the communication unit 1152 may include an output port for receiving one or more wires for communicating signals to other system components. Additionally or alternatively, communication unit 1152 may include any appropriate wireless communication components, In some embodiments, communication unit 1152 is in wired or wireless communication with an intravascular processing engine (e.g., 112). The intravascular processing engine may receive a signal from the communication unit 1152 representative of the signal from pickup 1150. In some such embodiments, the intravascular processing engine may associate signals received from the communication unit 1152 with one or more positions or changes in position of the magnetizable portion of the catheter 1102. That is, as a portion of the catheter 1102 (e.g., drive cable of an IVUS catheter or proximal portion of an MPS catheter) having magnetic domains (e.g., 1170) moves through the valve 1109 and past the pickup 1150, signals output from the pickup 1150 may be communicated to the intravascular processing engine via communication unit 1152.

In some embodiments, valve 1109 may include a power supply such as a battery 1154 to provide power for one or more of the pickup 1150 and the communication unit 1152. In an exemplary embodiment, battery 1154 is configured to provide the bias voltage (V_bias) for a pickup such as shown in FIG. 10. While shown in FIG. 11 as being a battery 1154, it will be appreciated that any variety of power sources may be used to power components in valve 1109, such as capacitive energy storage devices or power delivered to the valve 1109 from an external source.

As described previously, in some examples, the system can include a dedicated position sensing assembly configured to house position sensor. FIG. 12 is a cross-sectional view of an exemplary position sensing assembly. In the illustrated embodiment, the position sensing assembly 1280 includes a groove 1243 for receiving an anchor 1203 of a catheter 1202. The engagement of anchor 1203 and groove 1243 may act to keep a portion of the catheter stationary relative to other components of the system. For example, in some embodiments, the anchor 1203 being engaged with groove 1243 may keep a sheath of an IVUS catheter in place while the drive cable moves the transducer relative thereto. Similarly, the anchor 1203 and groove 1243 may act to keep a guidewire of an MPS system in place while the sensor delivery device and sensor are moved relative thereto.

In the illustrated embodiment, the catheter 1202 further includes a cable 1268 extending proximally through the position sensing assembly 1280 to a connector 1285 for interfacing with an attachment point 1256, for example, of an intravascular processing engine. In some embodiments, cable 1268 may include any of a variety of catheter 1202 components configured to move relative to the anchor 1203. For example, cable 1268 may include a drive cable of an IVUS catheter or the proximal portion of a sensor delivery device of an MPS system.

In the embodiment of FIG. 12, the cable 1286 includes magnetic domains 1270 such as described elsewhere herein. Magnetic domains 1270 may have a variety of magnetization magnitudes and directions, such as those illustrated in FIGS. 9A-C. During an intravascular operation, as a sensor (e.g., IVUS transducer or MPS pressure sensor) is moved through a patient's vasculature, cable 1268 may move through the position sensing assembly 1280.

For example, connector 1285 may engage a patient interface module (PIM), which provides an electromechanical interface between the intravascular processing engine and the catheter 1202. In some examples, PIM may be a part of the intravascular processing engine (e.g., 112) and/or the interface element (e.g., 110) in the system of FIG. 1. The PIM may be capable of translating (e.g., via translation mechanism, manual operation, etc.), thereby causing a portion of the catheter 1202 (e.g., cable 1268 and an associated intravascular sensor) to translate within the patient's vasculature. In such embodiments, translation of the PIM may result in movement of the magnetic domains 1270 through the position sensing assembly 1280.

The position sensing assembly 1280 may further include a pickup 1250 configured to detect the magnetic domains 1170 of the catheter 1202. In some embodiments, pickup 1250 may be similar to pickup 1050 in FIG. 10. In other embodiments, pickup 1250 may be any appropriate sensor capable of detecting magnetic fields from magnetic domains 1270, such as a Hall Effect sensor and the like. In some embodiments, the position sensing assembly 1280 includes a shielding element 1255 positioned proximate the pickup 1250 for preventing the pickup 1250 from sensing undesirable magnetic fields. Shielding 1255 may comprise any appropriate shielding material, such as an electrically conductive material. In some embodiments, shielding 1255 may be electrically coupled to a reference or ground potential relative to the pickup 1250.

Similar to the valve 1109 of FIG. 11, the position sensing assembly 1280 may include a communication unit 1252 for receiving signals from the pickup 1250. Communication unit 1252 may be configured to communicate signals to other system components (e.g., intravascular processing engine) representative of the signals received from the sensor via wired or wireless communication. The position sensing assembly 1280 may include a battery 1254 and/or other appropriate power source for providing electrical power to one or both of the pickup 1250 and the communication unit 1252

Figure 13A:
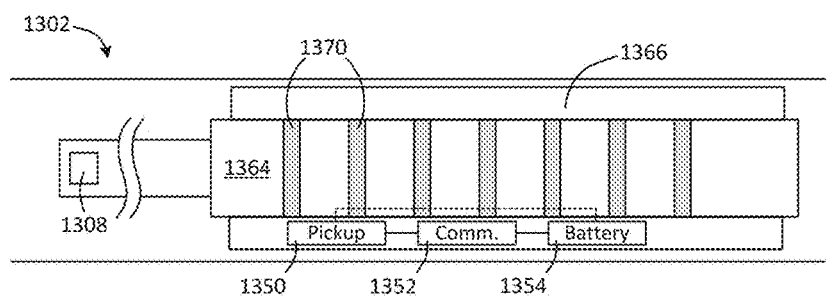
FIGS. 13A and 13B are illustrative configurations of first and second telescoping portions as part of an intravascular catheter that can be used in intravascular system.
Figure 13B:
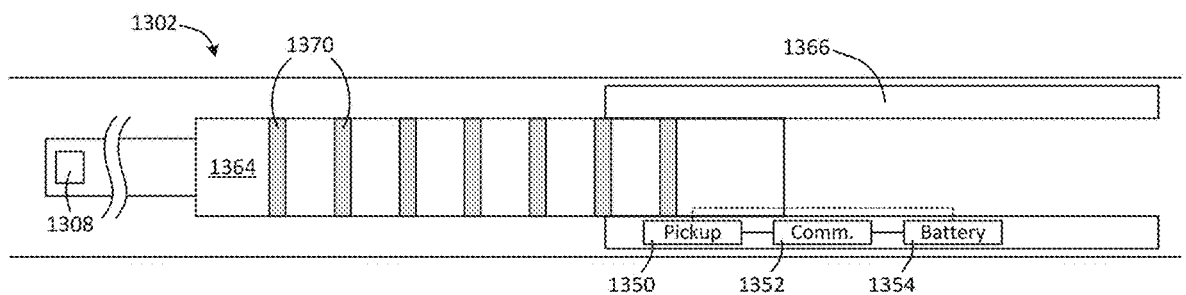

In some embodiments, the catheter 102 can comprise first and second telescoping portions, configured to telescope relative to one another in order to facilitate motion of the transducer 108. Telescoping portions can be used, for example, in conjunction with an anchor portion (e.g., 1203 in FIG. 12) of the catheter and the groove (e.g., 1243 in FIG. 12) disposed in a variety of locations of the system, such as an interface element (e.g., 110 in FIG. 1) to facilitate movement of a part of the catheter and intravascular sensor with respect to a stationary part of the catheter (e.g., the anchor 1203 of FIG. 12). FIGS. 13A and 13B are illustrative configurations of first and second telescoping portions 1364, 1366 as part of an intravascular catheter 1302 that can be used in intravascular system. FIG. 13A shows a first telescoping portion 1364 and a second telescoping portion 1366 as part of an intravascular catheter 1302. It will be appreciated that, while shown as part of catheter 1302 in the illustrated embodiments, telescoping portion can be external to the catheter in some systems. In the example shown in FIG. 13A, the first telescoping portion 1364 recessed into an opening within the second telescoping portion 1366. The first and second telescoping portions 1364, 1366 can be slidably coupled to allow relative movement therebetween.

FIG. 13B shows the first and second telescoping portions 1364, 1366 of the intravascular catheter 1302 of FIG. 13A, with the first telescoping portion 1364 extending from the second telescoping portion 1366. In many embodiments, the first and second telescoping portions 1364, 1366 can be configured to transition freely between the configurations shown in FIGS. 13A and 13B. That is, the first and second telescoping portions 1364, 1366 can "telescope" relative to one another. In some embodiments, one of the first and second telescoping portions 1364, 1366 can be fixed to a component of the intravascular system that remains stationary relative to the patient, such as a stationary portion of a translation mechanism.

In some embodiments, the intravascular sensor 1308 (e.g., IVUS transducer, MPS pressure sensor, etc.) can be coupled to one of the first and second telescoping portions 1364, 1366 and not the other. In such arrangements, the telescoping portion not coupled to the sensor 1308 can remain fixed while the other telescoping portion moves relative thereto, thereby causing motion of the sensor 1308 relative to the stationary telescoping portion. Thus, the telescoping motion of the first and second telescoping portions 1364, 1366 can facilitate motion of the sensor 1308. In an illustrative embodiment, the sensor 1308 is coupled to the first telescoping portion 1364 while the second telescoping portion 1366 is fixed to a stationary component of the system. As motion of the sensor 1308 is actuated (e.g., via manual translation, motorized translation, etc.), the first telescoping portion 1364 can translate within the second telescoping portion 1366. In some embodiments, the sensor 1308 can be coupled to the second telescoping portion 1366 while the first telescoping portion 1364 is fixed to a stationary component of the system. As motion of the sensor 1308 is actuated (manual translation, motorized translation, etc.), the second telescoping portion 1366 can translate on the outside of the first telescoping portion 1364. In various configurations, the sensor 1308 can be coupled to the first 1364 or second 1366 telescoping portion via a drive cable or a proximal portion of a sensor delivery device. Alternatively, in some systems, the first 1364 or second 1366 telescoping portion can be a part of the drive cable or the proximal portion of the sensor delivery itself.

In some embodiments, the relative movement of the first and second telescoping portions 1364, 1366 of the catheter 1302 can be correlated to the motion of the sensor 1308 within a patient's vasculature. In some such examples, one of the first 1364 and second 1366 telescoping portions may include magnetic domains 1370 while the other includes a pickup capable of sensing the position and/or movement of magnetic domains. In the illustrated embodiment, the first telescoping portion 1364 includes a plurality of magnetic domains 1370, for example, such as those described with regards to FIGS. 9A-C, 11, and 12. As described above, magnetic domains 1370 may include a variety of magnetization directions and/or magnitudes that may be used to differentiate the domains as they move past pickup 1350. Similar to embodiments described above, magnetic domains 1370 may be integral into the material of the first telescoping portion 1364 or may be formed in a magnetizable coating disposed on the first telescoping portion 1364.

Accordingly, in some such embodiments, movement of the first telescoping portion 1364 relative to the second telescoping portion 1366 (e.g., between the illustrated configurations of FIGS. 13A-B) and motion of the sensor 1308 within the patient results in motion of the magnetic domains 1370 relative to pickup 1350 located in the second telescoping portion 1366. Thus, the magnetic field experienced by pickup 1350 varies as the sensor 1308 moves within the patient. As described with regard to other embodiments, the pickup 1350 may output a signal representative of the experienced magnetic field. Since the magnetic field changes with respect to the position of the sensor 1308, the changes in the signal output from the pickup 1350 may be representative of changes in the sensor 1308 position. The signals output from the pickup 1350 may be received by a communication unit 1352 configured to communicate the signals received from the pickup 1350 or signals representative thereof to the intravascular processing engine. Thus, in some such examples, the intravascular processing engine receives signals from the communication unit 1352 representative of the position and/or changes in position of the sensor 1308 within the patient. In the illustrated embodiment, the second telescoping portion 1366 includes a battery 1354 for providing electrical power to one or more of the pickup 1350 and the communication unit 1352. Battery 1354 can include any variety of power sources for providing such electrical power, and can be similar to batteries 1154 and 1254 described with respect to FIGS. 11 and 12, respectively.

It will be appreciated that, while magnetic domains 1370 are shown as being disposed on the first telescoping portion 1364 and pickup 1350, communicating unit 1352, and batter 1354 on the second telescoping portion 1366, alternative configurations are possible. For example. magnetic domains may be positioned on the second telescoping portion 1366 while pickup 1350, communicating unit 1352, and batter 1354 are disposed on the first telescoping portion 1364. Additionally or alternatively, communication unit 1352 and battery 1354 need not be included on the same portion of pickup 1350. In general, each of communication unit 1352 and battery 1354 may be positioned on the first 1364 or second 1366 telescoping portions independent of the location of the other and of the locations of pickup 1350 and magnetic domains 1370.

It will be appreciated that, while the illustrated embodiments show shaded magnetic domains (e.g., 1170, 1270, 1370) having blank space therebetween, the domains need not be separated by unmagnetized spaces. In some examples, space between the illustrated, shaded magnetic domains may also include magnetic domains, for example, having different magnetizations than adjacent, shaded magnetic domains Additionally or alternatively, neighboring shaded magnetic domains have distinguishable magnetizations from one another. In still further embodiments, magnetic domains may be separated from one another by non-magnetic material, or may be immediately adjacent to one another.

As described, in various embodiments, the intravascular processing engine is configured to receive a signal from a communication unit (e.g., 1152, 1252, 1352) indicative of the position and/or motion of magnetic domains relative to a pickup (e.g., the pickup of FIG. 10 or other magnetic sensing element, such as a Hall Effect sensor, etc.). The signal received by the intravascular processing engine may include a signal produced by the pickup, or may be a signal different from, but based on, the signal produced by the pickup. For example, the communication unit may be configured to output a signal to the intravascular processing engine based on whether or not the magnetic field at the pickup is greater than any number of threshold values.

The communication unit may be configured to transmit the signal to the intravascular processing engine via wired or wireless transmission. The intravascular processing engine may receive the signal from the communication unit and, based on the received signal, determine position information associated with the position of an intravascular sensor within a patient.

Position information may be indicative of a relative or absolute position of the sensor within a patient's vasculature. As described elsewhere herein, varying magnetization magnitudes and directions of the magnetic domains results in the domains being distinguishable from one another. Thus, changes in the magnetic field present at the pickup are indicative of changes in the magnetic domains proximate the pickup, and thus, in some embodiments, motion of the sensor within the patient. Combining information regarding the size and spacing of magnetic domains with detected changes in the magnetic field at the pickup (i.e., changes in positions of magnetic domains) may be used to determine the amount of motion of the magnetic domains.

As discussed above, in some embodiments, magnetic domains may be arranged so that the direction of motion of the domains (and thus a portion of the catheter) may be determined. For example, domain magnetization magnitudes arranged in a repeating order of low, medium, and high may be used. In such an example, a low-magnitude domain followed by a medium-magnitude domain indicates motion in a first direction, while a low-magnitude domain followed by a high-magnitude domain indicates motion opposite the first direction. Additionally or alternatively, a plurality of pickup elements may be employed in order to detect if magnetic domains are moving in one direction or another.

In some examples, the intravascular processing engine may associate position information with corresponding sensor information. The combined position and sensor information may be used to generate longitudinal data, such as the longitudinal IVUS image of FIG. 4 or the MPS pressure-distance curve in FIG. 7. Such information may be useful in better diagnosing a patient's condition, including determining the location of a lesion or other feature within the blood vessel. Additionally or alternatively, associated position and sensor information may allow for improved and localized therapy. For example, associated position and sensor information may allow a clinician to both locate a severe lesion within a blood vessel (e.g., location 700 in FIG. 7) and also to accurately position a stent in an optimal position for treating the lesion.

Various configurations have been described. Position information acquired from a position sensor associated with magnetic domains disposed on or proximate a catheter may be acquired by the intravascular processing engine for associating with corresponding sensor information. In various embodiments, such position information may be associated with image data acquired from an IVUS transducer or pressure data acquired from a pressure sensor (e.g., an MPS). Resulting sets of associated data (e.g., position and image data, position and pressure data, etc.) may be used to generate sets of data such as an IVUS longitudinal image (e.g., 426 in FIG. 4) or a pressure-position plot (e.g., plot of FIG. 7). Such information may be used by the system operator to more precisely analyze the status of a patient. This may allow for a more detailed diagnosis and a more precisely defined treatment plan. In some cases, the data may be used to determine a most effective treatment location within the patient, and in some further examples, to execute a treatment at the determined location.

Various aspects of the invention can be embodied in a non-transitory computer-readable medium. A non-transitory computer-readable medium can comprise executable instructions for causing a processor to receive sensor information from a sensor (e.g., 108) located near the distal end (e.g., 106) of an intravascular catheter (e.g., 102), and position information from a position sensor (e.g., including one or more magnetic domains). The position sensor can comprise a movable element and a reference element and the position information can comprise a movable element position, representing the position of the movable element relative to the reference element and correlated to the sensor position. The non-transitory computer-readable medium can further contain executable instructions to cause the processor to associate sensor information with position information corresponding to the location at which the sensor information was acquired. In some embodiments, the non-transitory computer-readable medium may generate a display based on the received sensor information and position information. For example, a longitudinal image comprising position information and corresponding image information from an IVUS catheter may be generated. In other examples, a pressure vs. distance curve comprising position information and corresponding pressure information from a pressure sensor (e.g., MPS) may be generated. In some embodiments, the non-transitory computer-readable medium can be embodied in the processing engine 112. In some embodiments, a non-transitory computer-readable medium can comprise executable instructions for causing a processor to perform any method discussed herein.

It should be appreciated that components described with regard to particular embodiments of the invention may be combined to form additional embodiments. Instructions embedded or encoded in a computer-readable storage medium may cause a programmable processor, or other processor, to follow the instructions prescribed. Computer readable storage media may include random access memory (RAM), read only memory (ROM), a hard disk, optical media, or other computer readable media.

Various embodiments have been described. Such embodiments are exemplary and do not limit the scope of the invention in any way. Rather, these and others are within the scope of the following claims.

The invention claimed is:

1. An intravascular system comprising:
a catheter including a proximal end, a distal end, a plurality of magnetic domains, a sensor located at the distal end, and a cable extending from the proximal end of the catheter to the distal end of the catheter and operatively connected to the sensor at the distal end, the sensor configured to provide sensor information representative of one or more intravascular properties of a patient, wherein the plurality of magnetic domains are consecutively arranged in a plurality of groups of magnetic domains, each group of magnetic domains having, consecutively arranged, one magnetic domain with a first magnetization magnitude, one magnetic domain with a second magnetization magnitude greater than the first magnetization magnitude, and one magnetic domain with a third magnetization magnitude greater than each of the first magnetization magnitude and the second magnetization magnitude, wherein the first magnetization magnitude in each group of magnetic domains is a same first magnetization magnitude, wherein the second magnetization magnitude in each group of magnetic domains is a same second magnetization magnitude, and wherein the third magnetization magnitude in each group of magnetic domains is a same third magnetization magnitude;
a magnetic pickup configured to output a pickup signal based on the magnetic field at the magnetic pickup produced by the plurality of magnetic domains; and
an intravascular processing engine in communication with the sensor of the catheter and the magnetic pickup and configured to:
(i) receive the sensor information from the sensor of the catheter;
(ii) receive a position signal representative of the pickup signal;
(iii) determine position information related to a position of the sensor located at the distal end based on the received position signal; and
(iv) combine the received sensor information and corresponding determined position information.

2. The system of claim 1, wherein the plurality of magnetic domains are disposed on the cable.

3. The system of claim 2, wherein the cable comprises a magnetizable material, and wherein the plurality of magnetic domains are included in the cable itself.

4. The system of claim 2, wherein the magnetic domains are included in a magnetizable coating applied to the cable.

5. The system of claim 2, further comprising a valve configured to interface with a patient and to receive the catheter so that the cable may translate longitudinally through the valve, and wherein the magnetic pickup is disposed in the valve.

6. The system of claim 5, wherein the valve comprises a hemostasis valve.

7. The system of claim 5, further comprising a communication unit disposed in the valve and configured to receive the magnetic pickup signal from the magnetic pickup and to communicate the position signal to the intravascular processing engine indicative of the received pickup signal via a wireless communication link.

8. The system of claim 2, wherein the catheter comprises an intravascular ultrasound (IVUS) catheter, the sensor of the catheter comprises an IVUS transducer, the cable comprises a drive cable,
and wherein the intravascular processing engine is configured to receive image information from the IVUS transducer and position information from the position sensor to generate a longitudinal IVUS image.

9. The system of claim 2, wherein the catheter comprises a monorail pressure sensor (MPS) catheter having a proximal portion, the sensor comprises a pressure sensor, and the cable comprises the proximal portion of a sensor delivery device,
and wherein the intravascular processing engine is configured to receive pressure information from the pressure sensor at a plurality of locations within a patient and position information from the position sensor associated with the pressure information at each of the locations.

10. The system of claim 2, further comprising a position sensing assembly configured to support the magnetic pickup and to receive a portion of the catheter so that the cable translates longitudinally relative to the position sensing assembly when the sensor is translated.

11. The system of claim 10, wherein the position sensing assembly comprises shielding positioned proximate the magnetic pickup for reducing noise at the magnetic pickup.

12. The system of claim 1, wherein the catheter further comprises a first telescoping portion and a second telescoping portion, the first telescoping portion configured to move within and relative to the second telescoping portion when the sensor moves within the patient, and wherein the plurality of magnetic domains is disposed on one of the first and second telescoping portions and the magnetic pickup is disposed to the other of the first and second telescoping portions.

13. The system of claim 1, wherein the magnetic pickup comprises a plurality of magneto-resistive elements.

14. A position sensing system for an intravascular catheter comprising:
a plurality of magnetic domains operatively coupled to a portion of the intravascular catheter, wherein the plurality of magnetic domains are arranged in a plurality of groups of magnetic domains, each group of magnetic domains having one magnetic domain with a first magnetization magnitude, one magnetic domain with a second magnetization magnitude greater than the first magnetization magnitude, and one magnetic domain with a third magnetization magnitude greater than each of the first magnetization magnitude and the second magnetization magnitude, wherein the first magnetization magnitude in each group of magnetic domains is a same first magnetization magnitude, wherein the second magnetization magnitude in each group of magnetic domains is a same second magnetization magnitude, and wherein the third magnetization magnitude in each group of magnetic domains is a same third magnetization magnitude;

at least one pickup positioned proximate to the at least one magnetic domain, the at least one pickup configured to output a signal representative of the magnetic field at the pickup due at least in part to the magnetic field caused by the plurality of magnetic domains; and an intravascular processing engine configured to receive a position signal based on the signal output from the at least one pickup, wherein the plurality of magnetic domains is operatively coupled to the intravascular catheter such that a position of each magnetic domain is correlated to a position of an intravascular sensor coupled to the catheter, and wherein the intravascular processing engine is configured to determine at least the relative position of the intravascular sensor based on the received position signal.

15. The system of claim 14, wherein the plurality of magnetic domains have known sizes, and wherein the intravascular processing engine is configured to determine an amount of motion of the intravascular sensor based on the received position signal and the known sizes of the plurality of magnetic domains.

16. The system of claim 14, further comprising a communication unit configured to receive the output signal from the at least one pickup and communicate a position signal to the intravascular processing engine based on the received output signal.

17. The system of claim 14, wherein the at least one pickup comprises a plurality of pickups, the plurality of pickups each configured to produce an output signal, and wherein the intravascular processing engine is configured to receive a plurality of position signals representative of respective output signals of each of the plurality of pickups.

18. The system of claim 17, wherein the intravascular processing engine is configured to determine an amount and direction of movement of the intravascular sensor based on the plurality of received position signals.

* * * * *